United States Patent
Heckmann et al.

(10) Patent No.: US 11,918,006 B2
(45) Date of Patent: Mar. 5, 2024

(54) WHEY PREPARATION FOR IMPROVING BRAIN DEVELOPMENT

(71) Applicant: Arla Foods Amba, Viby J. (DK)

(72) Inventors: Anne Birgitte Lau Heckmann, Viby J. (DK); Kristian Raaby Poulsen, Viby J. (DK); Hans Bertelsen, Viby J. (DK); Anders Daniel Andersen, København N (DK); Thomas Thymann, Kirke Eskildstrup (DK)

(73) Assignee: ARLA FOODS AMBA, Viby J (DK)

( * ) Notice: Subject to any disclaimer, the term of this patent is extended or adjusted under 35 U.S.C. 154(b) by 332 days.

(21) Appl. No.: 16/099,744

(22) PCT Filed: May 15, 2017

(86) PCT No.: PCT/DK2017/050151
§ 371 (c)(1),
(2) Date: Nov. 8, 2018

(87) PCT Pub. No.: WO2017/194068
PCT Pub. Date: Nov. 16, 2017

(65) Prior Publication Data
US 2019/0133144 A1    May 9, 2019

(30) Foreign Application Priority Data
May 12, 2016 (EP) .................... 16169410

(51) Int. Cl.
A23C 9/142 (2006.01)
A23C 21/00 (2006.01)
A23J 1/20 (2006.01)
A23K 20/147 (2016.01)
A23K 50/30 (2016.01)
A23K 50/60 (2016.01)
A23L 33/00 (2016.01)
A23L 33/19 (2016.01)
A61K 35/20 (2006.01)
A61K 38/17 (2006.01)

(52) U.S. Cl.
CPC .......... *A23C 9/1425* (2013.01); *A23C 9/1427* (2013.01); *A23C 21/00* (2013.01); *A23J 1/205* (2013.01); *A23K 20/147* (2016.05); *A23K 50/30* (2016.05); *A23K 50/60* (2016.05); *A23L 33/19* (2016.08); *A23L 33/40* (2016.08); *A61K 35/20* (2013.01); *A61K 38/1709* (2013.01); *A23C 2210/206* (2013.01); *A23V 2002/00* (2013.01)

(58) Field of Classification Search
CPC ..... A23C 9/1425; A23C 9/1427; A23C 21/00; A23C 21/02; A23C 9/12; A23L 33/19; A23L 33/40; A23J 1/205
See application file for complete search history.

(56) References Cited

U.S. PATENT DOCUMENTS

| | | | | |
|---|---|---|---|---|
| 3,882,256 A | * | 5/1975 | De Boer | .................. A21D 2/26 530/832 |
| 4,497,836 A | | 2/1985 | Marquardt | |
| 5,707,678 A | * | 1/1998 | Gregory | .............. A23C 9/1425 426/422 |
| 5,756,680 A | | 5/1998 | Ahmed | |
| 6,120,820 A | * | 9/2000 | Brody | .................. A23C 9/1425 426/258 |
| 2005/0276904 A1 | * | 12/2005 | Brown | .................. A23C 20/00 426/656 |
| 2006/0240115 A1 | * | 10/2006 | Kanamaru | .............. A61P 31/14 424/535 |
| 2012/0201839 A1 | * | 8/2012 | Penttla | .................... A23L 33/40 424/184.1 |

FOREIGN PATENT DOCUMENTS

| | | |
|---|---|---|
| WO | WO 94/13148 | 6/1994 |
| WO | WO 2011/051557 | 5/2011 |
| WO | WO 2015/086789 | 6/2015 |

OTHER PUBLICATIONS

Andersen, Anders D., et al. "Delayed growth, motor function and learning in preterm pigs during early postnatal life" Am. J Physiol Regul Integr Comp Physiol 310: R481-R492, 2016.
Heino et al. "Functional properties of native and cheese whey protein concentrate powders" Intl. Journal of Dairy Technology, vol. 60, No. 4, Nov. 2007, pp. 277-285.
Li et al. "Whey protein processing influences formula-induced gut maturation in preterm pigs" The Journal of Nutrition 2013/09/18/ nj.113.182931.
International Search Report and Written Opinion for PCT/DK2017/050151 dated Jul. 5, 2017, 10 pages.
Teknotext AB (Editor), "Tetra Pak Dairy Processing Handbook," Chapter 14, pp. 287-301, Tetra Pak Processing Systems AB, 1995.
Niciforovic, A. et al."Detection of irradiated food by the changes in protein molecular mass distribution," Radiation Physics and Chemistry_ 55_1999, pp. 731-735.

* cited by examiner

*Primary Examiner* — Jeffrey P Mornhinweg
(74) *Attorney, Agent, or Firm* — Casimir Jones SC; Lisa Mueller

(57) ABSTRACT

The present invention relates to a bioactive sweet whey protein concentrate or composition for increasing e.g. cognitive functions particularly in young mammals such as pre-term or term infants, toddlers, children or young adults. The present invention further disclose a new concept for large-scale industrial production method of bioactive whey protein concentrates or compositions by use of mild heat treatment and pressure driven membrane separation.

14 Claims, 14 Drawing Sheets

WHEY PREPARATION FOR IMPROVING BRAIN DEVELOPMENT

FIELD OF THE INVENTION

The present invention relates to a bioactive sweet whey protein concentrate or preparation for increasing the brain development and thereby cognitive functions particularly in young mammals such as preterm or term infants, toddlers, children or young adults. The present invention further disclose new routes for large-scale production methods of bioactive whey protein concentrates and preparations.

BACKGROUND OF THE INVENTION

Whey contains various bioactive components that demonstrate a large range of desired properties, such as reducing the risk of metabolic syndrome, which can lead to various chronic diseases, cardiovascular disease, diabetes, treatment of cancers affecting the immune system, health problems associated with HIV, hepatitis B and osteoporosis have also been reduced, either directly or indirectly, by the use of whey components.

Currently scientific and commercial interest is focused on the biological properties and nutritional value of whey protein concentrates. Products such as infant and hypoallergenic foods and sports drinks have prompted the selection and development of methods for isolating and concentrating individual whey proteins or a set protein in a purified or enriched form, i.e., whey protein concentrates (WPC) or protein isolates (WPI), and WPCs have been shown to provide health benefits to humans of all ages by providing specific bioactive components above and beyond those necessary for nutrition.

To produce WPCs, many different production process steps can be applied, and each of these processes e.g. whey separation from fresh milk, heat-treatment, filtration, spray-drying etc. may cause a significant reduction of many bioactive proteins present in WPCs.

These methods typically rely on denaturation (salt treatment processes, heat and pH treatments), ionic selection (electrophoresis, ion-exchange chromatography), selection according to shape and size (membrane filtration, gel permeation and size-exclusion chromatography), polarity (high-performance liquid chromatographic), chemical reactivity (complexation) and physical properties (concertation, foaming and freeze-drying).

Some of these processes have not been widely implemented for largescale separation because of their complexity, high cost, low overall yield, poor selectivity, low product activity, or product degradation associated with the extremes of heat, pH and salt used during the process.

Membrane separation processes, such as ultrafiltration (UF), reverse osmosis (RO) and ultrafiltration with diafiltration (DF) in particular, are now industrially applied in the manufacture of ordinary whey powder and WPCs with protein contents of 30-80%. An example of such is Arla's WPC 80 (Lacprodan® DI-8090).

Gel filtration and ion-exchange chromatography techniques are also employed in the manufacture of WPIs with protein contents of 90-95%, but the whey protein content of these isolates is not always up to this level.

Precipitation methods are often used at the laboratory scale to obtain whey protein concentrates and produce peptides; however, the chemical composition and functionality of whey protein preparations and peptides are affected by the method used in the proteins concentration process. Chemical additives and factors, such as pressure, temperature, agitation rate and holding time, have been shown to affect solvent pH, protein conformation and yield.

In particular, protein purity can be critical for the biological activity of concentrated products. In addition, the biological properties of the concentrated products are difficult to standardise due to the complex nature of the bioactivities exerted by different whey proteins.

The present inventors have previously investigated effects of different types of acid whey compositions, e.g. Yanqi Li et al., The Journal of Nutrition 2013, showing that whey protein processing influences formula-induced gut maturation in preterm pigs. The preparation Yanqi Li et al. used for their measurement of gut maturational effects where based entirely on acid whey preparations.

WO2015086789 relates to use of modified sweet whey for promoting the postnatal development of the infant central nervous system and treatment of disorders associated with delayed establishment of cognitive function or cognitive function impairment in a young animal. The modified sweet whey protein of WO2015086789 is characterised in that some or all of the caseino-glyco-macropeptide (CGMP) has been removed.

However, at present concentrated products are extremely difficult to standardise due to the complex nature of the activities exerted by different whey proteins, and there is no standard of identity for WPCs. There also are no compositional standards (e.g., minimum or maximum standards for the protein content), and yet, there is a need for identifying whey compositions having superior functional effects.

The present inventors here disclose a new bioactive WPC composition with superior effects on physical activities and motoric control, and methods of its production.

SUMMARY OF THE INVENTION

The globular structure of whey protein makes them heat labile. Heat treatment of the whey proteins above 60° C., results in unfolding of the globular structure and the proteins thereby denature. Thus, going beyond a process temperature of 60° C. will generate denaturated proteins in the industrial manufacturing processes of WPC.

The present inventors disclose a range of industrial methods with various sequential steps for manufacturing WPC with less denaturated proteins and improved functionality. The basic concept is to use less heat treatment than typically applied in industrial settings, combined with a range of precise sequential steps including separation, filtration and optionally drying steps that secures the balance of gentle treatment of the whey to ensure that the bioactivity of the WPC is maintained along the need of various sequential industrial steps like e.g. the filtering.

The present inventors provide in a first aspect, a method for producing a sweet whey preparation comprising the sequential steps of
  a) providing a sweet whey
  b) applying a heat treatment of less than 68° C. for less than 20 seconds,
  c) applying a separation,
  d) applying a micro filtration on the retentate from step c)
  e) applying a separation on the permeate from step d),
  f) applying a heat treatment of less than 65° C. for less than 20 seconds on the retentate of step e)
  g) optionally, cooling the product obtained in f) to less than 15° C., and
  h) optionally drying said product
thereby obtaining a sweet whey preparation.

In another aspect, the present inventors disclose a method for producing a sweet whey preparation comprising the sequential steps of
- a) providing a sweet whey
- b) applying a micro filtration and/or applying a heat treatment of less than 68° C. for less than 20 seconds
- c) applying a separation and/or concentration on the permeate from step b),
- d) applying a heat treatment of no less than 72° C. for less than 15 seconds on the retentate of step c), if the total dry solids is less than 17.5% and the protein lactose ration is less than 0.3
- e) applying a separation,
- f) optionally applying a micro filtration on the retentate from step e)
- g) applying a heat treatment of less than 65° C. for less than 20 seconds on the retentate of step e) or f)
- h) optionally, cooling the product obtained in g) to less than 15° C., and
- i) optionally drying said product thereby obtaining a sweet whey preparation.

In a third aspect, the present inventors disclose a method for producing a sweet whey preparation comprising the sequential steps of
- a) providing a sweet whey
- b) applying a separation and/or concentration step,
- c) applying a micro filtration and/or applying a heat treatment of less than 68° C. for less than 20 seconds,
- d) applying a heat treatment of no less than 72° C. for less than 15 seconds on the retentate of step c),
- e) applying a separation,
- f) optionally applying a micro filtration on the retentate from step e),
- g) applying a heat treatment of less than 65° C. for less than 20 seconds on the retentate of step e) or f),
- h) optionally, cooling the product obtained in h) to less than 15° C., and
- i) optionally drying said product, thereby obtaining a sweet whey preparation.

While the sweet whey preparations obtained from the methods disclosed herein seeks to maintain the proteins in their native state as a basic concept, they thus share a wide range of features such as their denaturation level, lactoferrin and IgG content to name a few.

Thus, a fourth aspect of the present invention relates to the products obtainable by the methods disclosed herein and the structural features they share.

There are many different whey preparations existing today, but for the present inventors the overall objective was to provide whey preparations with improved functional effects over conventionally produced whey preparations.

Thus, one aspect of the invention relates to a sweet whey preparation obtainable by any of the methods disclosed herein.

Another aspect of the present invention relates to the use of the sweet whey preparation obtainable by any of the methods disclosed herein.

The present inventors have developed and tested these sweet whey preparations in a preterm neonates piglet model, and the products of the present invention where thereby shown to have positive effect on e.g. health and development of infants, especially preterm, small for gestational age, low birth, very low and extremely low birth weight infants.

Thus, a particular interesting aspect of the invention relates to the specific use of the sweet whey preparations disclosed herein for the administration directly to an infant or young child in its pure form, or diluted in water or breast milk, in a food supplement, or together with in a milk fortifier, or any milk support used during trophic feeding, in an infant formula, or in a milk based drink.

DETAILED DESCRIPTION OF THE INVENTION

The present invention relates to methods for producing whey protein concentrates, which are particularly useful for young mammals who are born prematurely, but in fact, the manufacturing process described herein generates whey protein concentrates with a wide range of nutritional supplement applications and therapeutic applications.

Whey is typically processed to yield whey protein in three forms: whey isolate, whey concentrate, or whey hydrolysate. The difference between the whey protein forms is the composition of the product, particularly the protein content. WPC Whey concentrates (WPC) typically have a low level of fat and cholesterol but, in general, have higher levels of bioactive compounds as well as carbohydrates in the form of lactose. The percentage of protein in WPC depends on how concentrated it is. Lower end concentrates tend to have 30% protein and higher end up to 90%.

An example of conventionally-heat-treated WPC is Lacprodan DI-8090, AFI—hereafter named ConWPC.

Whey Preparation—Sequential Type A

In one embodiment, the present invention relates to a method for producing a sweet whey preparation [BIOWPC] comprising the sequential steps of
- a) providing a sweet whey
- b) applying a heat treatment of less than 68° C. for less than 20 seconds,
- c) applying a pressure driven membrane separation,
- d) applying a micro filtration having a particle size of max 2 μm on the retentate from step c),
- e) applying a pressure driven membrane separation on the permeate from step d),
- f) applying a heat treatment of less than 65° C. for less than 20 seconds on the retentate of step e),
- g) optionally, cooling the product obtained in f) to less than 15° C., and
- h) optionally, drying said product, thereby obtaining a sweet whey preparation.

In another embodiment, the present invention relates to a method for producing a sweet whey preparation [BIOWPC] comprising the sequential steps of
- a) providing a sweet whey
- b) applying a heat treatment of 63° C. for 15 seconds, and cooling the sweet whey to 5° C.
- c) applying a ultrafiltration at 10° C. with a feed pressure at 3.0 bar and a pressure drop per membrane element at 1.0 bar,
- d) applying a micro filtration having a particle size of 1.4 μm on the retentate from step c), at 15° C. and having the TMP at 1.5 bar and the VCF is set to 50
- e) applying a second ultrafiltration at 10° C. with a feed pressure at 3.0 bar and a pressure drop per membrane element at 1.0 bar, on the permeate from step d),
- f) applying a heat treatment of less than 63° C. for 15 seconds on the retentate of step e),
- g) optionally, cooling the product obtained in f) to less than 15° C., and
- h) spray drying said product, thereby obtaining a sweet whey preparation.

WPI

Whey (WPI) isolates typically contain a higher percentage of pure protein and can be pure enough to be virtually lactose free, carbohydrate free, fat free, and cholesterol free. WPI is usually at least 90% protein.

WPH

Whey protein hydrolysate (WPH) is whey protein that has undergone at least partial hydrolysis—a process necessary for the body to absorb protein. WPH does not require as much digestion as the other two forms of whey protein. WPH, it is commonly used in medical protein supplements and infant formulas because of it's improved digestibility and reduced allergen potential.

The present invention especially focus on the differences in the processing. Industrial processing results in products that differs from conventional whey concentrate in several important ways, and it is an objective of the present invention to provide a WPC having higher levels of bioactive compounds compared to conventional industrial processing. The WPC of the present invention is thus named Bioactive WPC or BIO WPC for short.

Acid Whey

Acid whey (also known as "sour whey") is a co-product produced during the making of acid types of dairy products such as cottage cheese or strained yogurt.

Acid whey is produced, when milk is acidified and the curd is separated into caseinate and acid whey. The acidification can either be done using a mineral acid or microbial acidification. When caseinate is wanted in industrial settings, the acidification is normally done on low pasteurize skim milk e.g. 72° C., for 15 Sec.

Acid whey do not contain the protein casein glyco macro peptide (CGMP).

A large difference in the composition between acid WPC and the Bioactive WPC of the present invention is the CGMP level that is absent in acid whey, and the content of glycosylated molecules present on CGMP.

In the manufacturing of an acid whey WPC, no heat treatment is done, when the pHs is low (below 4.6). Before drying the pHs is adjusted to 7.5 and a heat treatment is performed before drying. The filtration steps may be similar to the Bioactive WPC produced. The process for production of whey powder (80 CV200) from acid whey involves:
1. Fines removal
2. First pressure driven filtration: UF membrane concentration to approximately WPC 35
3. Second filtration: Microfiltration reduce the bacterial count in WPC 35
4. Third pressure driven filtration: UF membrane concentration to WPC 80
5. pHs adjustment (pHs 7.5)
6. Heattreatment 66° C. 15 sec, (just before spray drying)
7. Spray drying Sweet Whey Sweet whey in the present context is whey produced during cheese production utilizing rennet. This is the case for hard cheese types like for example cheddar or Swiss cheese.

During cheese production rennet is added to cause the casein to precipitate. Rennet contains the enzyme chymosin which cleaves K-casein to para-K-caseinate and glycomacropeptide (CGMP), which is found in the sweet cheese whey. The whey is then separated from the cheese curd.

BIOWPC

The WPC of the present invention has higher levels of bioactive compounds compared to conventional industrial processed WPC preserved by reduced thermal processing and sequential steps as disclosed below. In the present context, then bioactivity can in particular be linked to specific effects such but not limited to the bioactivity markers in Example 6, the clinical outcomes in Example 7, the functions and activities in Example 8, the morphology of Example 9 and effects of Example 10 and the physical activity in Example 11 or any other effects disclose hereon.

The WPC of the present invention is a preparation obtained by the removal of sufficient nonprotein constituents from the whey so that the finished dry product contains not less than 25 percent protein.

The WPC of the present invention is produced by physical separation techniques such as precipitation, filtration, or dialysis. As with whey, whey protein concentrate can be used as a fluid, concentrate, or dry product form. The acidity of whey protein concentrate may be adjusted by the addition of safe and suitable pH-adjusting ingredients.

In one embodiment, the WPC of the present invention lives up to the US Code of Federal Regulations: Title 21, Volume 3, Revised as of Apr. 1, 2015, CITE: 21CFR184.1979c.

In another embodiment, the WPC of the present invention lives up to the US Code of Federal Regulations: Title 21, Volume 3, Revised as of Apr. 1, 2015, CITE: 21CFR184.1979c, with the exception that the WPC shall not be derived from milk that has been pasteurized, or the WPC shall not be subjected to pasteurization techniques or its equivalent before use in food, however the WPC shall use other means than temperatures above 68° C. to control the microbiology and/or safety of a product for human consumption.

Manufacturing BIOWPC

Heat treatment is commonly applied to whey during industrial processing in order to ensure the microbial safety of dairy products as well as to extend shelf. Whey protein denaturation is one of the main effects of heating which causes modification of the chemical and nutritional properties of the whey.

Depending on the physicochemical conditions in whey, the denaturation process is either reversible, where partial unfolding of the whey proteins takes place with a loss of helical structure, or irreversible where an aggregation process occurs involving sulfhydryl (—SH)/disulfide (S—S) interchange reactions and other intermolecular interactions, such as hydrophobic and electrostatic interactions.

These denaturation and aggregation reactions based on the processing of the whey in industrial settings are of considerable interest to dairy industry because knowledge of them is essential for devising ways to manipulate the chemical and nutritional properties of dairy products.

The present inventors disclose approaches to preventing or reducing denaturation and aggregation of whey proteins.

Whey Preparation—Sequential Type B

In another embodiment, the present invention relates to an alternative method for producing a sweet whey preparation [BIOWPC] comprising the sequential steps of
  a) providing a sweet whey,
  b) applying a micro filtration having a particle size of max 2 μm and/or applying a heat treatment of less than 68° C. for less than 20 seconds,
  c) applying a pressure driven membrane separation and/or reverse osmosis concentration on the permeate from step b),
  d) applying a heat treatment of no less than 72° C. for less than 15 seconds on the retentate of step c), if the total dry solids is less than 17.5% and the protein lactose ratio is less than 10, e) applying a pressure driven membrane separation,
f) optionally applying a micro filtration having a particle size of max 2 μm on the retentate from step e),
g) applying a heat treatment of less than 65° C. for less than 20 seconds on the retentate of step e) or f),
h) optionally, cooling the product obtained in g) to less than 15° C., and
i) optionally drying said product, thereby obtaining a sweet whey preparation.

Total Dry Solids

The US FDA have in their Code of Federal Regulations listed that whey protein concentrate shall be derived from milk that has been pasteurized, or the whey protein concentrate shall be subjected to pasteurization techniques or its equivalent before use in food. If such regulatory demand must be obliged, then the pasteurization techniques could be 72° C./15 s.

Thus, the present inventors provides means for such regulatory demand by applying a heat treatment of no less than 72° C. for less than 15 seconds on the retentate of step c), if the total dry solids is less than 17.5% and the protein lactose ratio is less than 10, because if the total dry solids exceeds 18% the regulatory demand to the pasteurization is 75° C./15 s, which according to the present invention may limit the functional effects of the BIO WPC.

Protein Lactose Ratio

In the present context, then the protein lactose ratio should be kept below 10, such as but not limited to less than 9, less than 8, less than 7, less than 6, less than 5, less than 4, less than 3, less than 2 or less than 1.

In one embodiment, the protein lactose ratio is less than 0.5, such as less than 0.4, less than 0.3, less than 0.2 or below.

Whey Preparation—Sequential Type C

In a further embodiment, the present invention relates to a method for producing a sweet whey preparation [BIO-WPC] comprising the sequential steps of
a) providing a sweet whey
b) applying a pressure driven membrane separation and/or reverse osmosis concentration,
c) applying a micro filtration having a particle size of max 2 μm and/or applying a heat treatment of less than 68° C. for less than 20 seconds,
d) applying a heat treatment of no less than 72° C. for less than 15 seconds on the retentate of step c),
e) applying a pressure driven membrane separation,
f) optionally applying a micro filtration having a particle size of max 2 μm on the retentate from step e),
g) applying a heat treatment of less than 65° C. for less than 20 seconds on the retentate of step e) or f),
h) optionally, cooling the product obtained in h) to less than 15° C., and
i) optionally drying said product, thereby obtaining a sweet whey preparation.

Providing a Sweet Whey

The amount of remaining whey during portioning is a decisive factor for the dry matter of the final product. This process can be exactly controlled with whey drainage drums and filter conveyors.

After whey drainage, cheese fines are removed and whey cream is also removed in a continues centrifugal separator.

The BIO WPC of the present invention is produced from whey drainage from cheese production.

In one embodiment, then the sweet whey is obtained from cheese production of Gouda type cheese, Mozzarella cheese and Cheddar cheese.

In one embodiment, the BIO WPC is produced from Gouda cheese production.

In one embodiment, the BIO WPC is produced from Mozzarella cheese production.

In one embodiment, the BIO WPC is produced from Cheddar cheese production.

In one embodiment, the cheese fines are removed in a Sweco vibrating sieve.

In order to preserve the higher levels of bioactive compounds in the BIO WPC compared to conventional industrial processed WPC, then it may be advantageously to make sure that the milk base of the sweet whey has not been exposed to standard industrial processing steps selected from the group consisting of thermal processing, ultra-high temperature processing (UHT), hydrolysis and irradiation.

In another embodiment, the milk base of the sweet whey has not been exposed to standard industrial processing steps selected from the group consisting of thermal processing higher than 72°/15 s, ultra-high temperature processing (UHT), hydrolysis and irradiation.

In another embodiment, the milk base of the sweet whey has not been exposed to standard industrial processing steps selected from the group consisting of thermal processing higher than 72°/15 s, ultra-high temperature processing (UHT), hydrolysis and irradiation.

In one embodiment, the milk base of the sweet whey has not been exposed to standard industrial processing steps selected from the group consisting of ultra-high temperature processing (UHT), hydrolysis and irradiation.

FIG. 1 show the whey drainage and processing at the cheese plant for Bioactive WPC.

First Heat Treatment

The first heat treatment in the methods of the present invention is performed in order to reduce cheese starter culture bacterial growth and preventing further pH drop in the whey. Typically, in industrial settings and also for regulatory purposes heat treatments are kept at elevated temperatures, and used for pasteurization and sterilization to secure the safety of the dairy product for human consumption and for extending the shelf life of the final product.

HTST

There are different pasteurization methods, but one of the most used is high-temperature, short-time heating (HTST), where the milk typically is heated to 72-80° C. for 15-30 s.

LTLT

Pasteurization at low temperature, long time (LTLT) at 63° C. for 30 min is also still used, but not to the same extent as HTST due to longer processing time, and it has been shown that HTST gives less chemical changes than LTLT heat treatment.

UHT

Ultrahigh temperature (UHT) heating is a sterilization process of milk which is used to destroy all microorganisms and spores in the milk and many enzymes are also inactivated. This is typically done by heating temperatures of 135-150° C. for 1-10 seconds.

A drawback of whey proteins is their instability to thermal processing, which leads to their denaturation, aggregation, and, under some conditions, gelation.

Increase in heating temperature and holding time will lead to an increase in whey protein denaturation, thus finding the balance on those two parameters is crucial.

Mild Heat Treatment

The present inventors applied a (first) heat treatment of less than 68° C. for less than 20 seconds. The heat treatment can be varied between 60-68° C. and still perform in order to reduce cheese starter culture bacterial growth and preventing further pH drop in the whey.

Thus, in one embodiment, the mild heat treatment of the present invention relates to heat treatment of less than 68° C., such as but not limited to less than 67° C., less than 66° C., less than 65° C., less than 64° C., less than 63° C., less than 62° C., less than 61° C., or less than 60° C.

In another embodiment, the holding time is kept at less than 20 seconds, such as but not limited to less than 19 seconds, less than 18 seconds, less than 17 seconds, less than 16 seconds, less than 15 seconds, less than 14 seconds, less than 13 seconds, less than 12 seconds, less than 11 seconds, or less than 10 seconds.

In one particular embodiment, the whey is heat treated at 63° C. for 15 sec. to reduce cheese starter culture bacterial growth and preventing further pH drop in the whey.

After the first heat treatment, the whey can be cooled to e.g. below 5° C., and stored in a silo tank before further processing. Typically, the whey of the present invention is stored for maximum 2 days, but this can be extended up to one week.

Separation Methods

There are several ways to separate or fractionate the whey of the present invention into specific components, such as but not limited to methods which rely on denaturation (salt treatment processes, heat and pH treatments), ionic selection (electrophoresis, ion-exchange chromatography), selection according to shape and size (membrane filtration, gel permeation and size-exclusion chromatography), polarity (high-performance liquid chromatographic), chemical reactivity (complexation) and physical properties (concertation, foaming and freeze-drying).

For the purpose of the present invention, then processes that have not been widely implemented for largescale separation because of their complexity, high cost, low overall yield, poor selectivity, low product activity, or particularly product degradation associated with the extremes of heat, pH and salt used during the process is of lesser interest.

Membranes provide physical barriers that permit the passage of materials only up to a certain size, shape or character.

Membrane separation processes, such as ultrafiltration (UF), reverse osmosis (RO) and diafiltration (DF) are all industrially applied in the manufacture of WPCs.

In one embodiment, then the separation step relates to a membrane separation process.

There are four crossflow, pressure-driven membrane separation processes currently employed for liquid/liquid and liquid/solid separation: ultrafiltration (UF), reverse osmosis (RO), nanofiltration (NF), and microfiltration (MF). Membranes are manufactured in a variety of configurations including hollow fibre, spiral, and tubular shapes. Each configuration offers varying degrees of separation.

Thus, in one embodiment, the separation steps of the BIO WPC manufacturing is made by pressure-driven membrane separation process selected from the group consisting of reverse osmosis, nanofiltration, ultrafiltration and microfiltration.

In one embodiment, the separation step is made by ultrafiltration.

Ultrafiltration

The membrane arrangements of the present invention is selected from the group consisting of tubular module, hollow fiber, spiral-wound module and plate and frame.

In one embodiment, the membrane arrangement is a spiral-wound module.

The ultrafiltration is applied in cross-flow.

Microfiltration

In one embodiment, the separation step is made by microfiltration.

If microfiltration is used, then both soluble proteins, salts and small molecules such as lactose are at least partly removed, whereas the insoluble whey protein particles are retained.

The microfiltration is applied in cross-flow.

Nanofiltration

In one embodiment, the separation step is made by nanofiltration.

If nanofiltration is used, only the smallest salts are at least partly removed.

In the present context, nanofiltration use a membrane filtration having pore size around 0.001 micron.

Reverse Osmosis

In one embodiment, the separation step is made by reverse osmosis.

The microfiltration is applied in cross-flow.

As in other membrane processes, the larger molecules that are retained in the membrane are referred to as the "retentate", and the smaller molecules that pass through the membrane become the "permeate".

First Pressure Driven Membrane Separation

Pressure has also been shown to have an impact on whey protein stability, thus maintain a correct pressure during the sequential steps of the present invention can be important for the bioactivity of the proteins.

In one embodiment, the first pressure driven membrane separation is an ultrafiltration.

Thus, in one embodiment, the whey is first concentrated into WPC 35 using a 5 or 10 Kd UF Spiral Wound membrane, wherein the temperature is kept in the range of 5-18° C., but could be as high as in the range of 45-55° C.—this is not used very often due to short run time because of bacteriological growth—and the feed pressure is in the range of 0.5-3.5 bar and a pressure drop per element ranging from 0.5 bar to 1.3 bar.

In another embodiment, the whey is concentrated into WPC 35 using a 5 Kd KOCH HKS 328 UF Spiral Wound membrane, and the temperature is kept at 10° C. and the feed pressure is 3.0 bar and the pressure drop per membrane element is 1.0 bar.

Micro-Filtration

The filters used in the microfiltration process of the present invention are specially designed to prevent particles such as, sediment, algae, protozoa or large bacteria from passing through a specially designed filter.

The typical particle size used for microfiltration ranges from about 0.1 to 10 µm.

In one embodiment the microfiltration has a particle size of max 2 µm, such as max 1.9 µm, max 1.8 µm, max 1.7 µm, max 1.6 µm, max 1.5 µm, max 1.4 µm, max 1.3 µm, max 1.2 µm, max 1.1 µm, 1.0 µm, max 0.9 µm, max 0.8 µm, max 0.7 µm, max 0.6 µm, max 0.5 µm, max 0.4 µm, max 0.3 µm, max 0.2 µm or max 0.1 µm.

In one embodiment the microfiltration has a particle size of 0.5 to 2 µm, such as 0.6 to 1.9 µm, 0.7 to 1.8 µm, 0.8 to 1.7 µm, 0.9 to 1.6 µm, 1.0 to 1.5 µm, 1.1 to 1.4 µm, 0.8 to 1.5 µm, 0.7 to 1.7 µm, 0.8 to 1.6 µm, or 1.0 to 2 µm.

In one embodiment, a second filtration reduces the bacterial count in the WPC 35. The bacterial reduction is performed using a Ceramic Membrane with a pore size ranging from 0.5 µm to 2.0 µm. The temperature is kept at 5-18° C. and the Trans Membrane Pressure (TMP) should be between 0.1 and 2.5 bar. The VCF is in the range of 2-100.

In another embodiment, the second filtration reduces the bacterial count in the WPC 35 retentate using a ceramic Tami 1.4 μm isoflux membrane. The filtration is performed at 15° C. and the TMP is 1.5 bar. The VCF is set to 50.

Concentration

In the present context, the term concentration relates to reverse osmosis or nano filtration.

Second Pressure Driven Membrane Separation

In one embodiment, the second pressure driven membrane separation is an ultrafiltration.

The present invention applies at least two different rounds of pressure driven membrane separation, and the second round further process the whey into WPC 80.

In one embodiment, the permeate from the ceramic filtration is further processed into WPC 80 using a 5 or 10 Kd UF Spiral Wound membrane.

An SW membrane that can be sanitized at temperatures above 70° C. is preferable in order to keep the high microbial status after MF filtration.

Thus, in one embodiment the filtration is made with a Spiral Wound membrane.

In one embodiment, the temperature during the second round of pressure driven membrane separation is in the range of 5-18° C., but could also be as high as in the range of 45-55° C., but higher temperatures is not used very often due to short run time because of bacteriological growth.

In one embodiment, the feed pressure is in the range of 0.5-3.5 bar, such as but not limited to a feed pressure is in the range of 1-3.5 bar, a feed pressure is in the range of 1.5-3.5 bar, a feed pressure is in the range of 2-3.5 bar, a feed pressure is in the range of 2.5-3.5 bar, or a feed pressure is in the range of 3.0-3.5 bar.

In one embodiment, the pressure drop per membrane element is 0.5 bar to 1.3 bar, such as but not limited to a pressure drop per membrane element of 0.6 bar to 1.3 bar, a pressure drop per membrane element of 0.7 bar to 1.3 bar, a pressure drop per membrane element of 0.8 bar to 1.3 bar, a pressure drop per membrane element of 0.9 bar to 1.3 bar, a pressure drop per membrane element of 1.0 bar to 1.3 bar, a pressure drop per membrane element of 1.1 bar to 1.3 bar, a pressure drop per membrane element of 1.2 bar to 1.3 bar, a pressure drop per membrane element of 0.8 bar to 1.2 bar, or a pressure drop per membrane element of 0.9 bar to 1.1 bar.

In one embodiment, the permeate from the ceramic filtration is further processed into WPC 80 using a 10 Kd KOCH hpht 131 UF Spiral Wound membrane, and during the production the temperature is 10° C. and the feed pressure is 3.0 bar, and the pressure drop per membrane element is 1.0 bar.

Before filtration, plant and membranes are sanitized at 70° C. just before filtration.

Second Heat Treatment

The present inventors applied a second heat treatment of less than 65° C. for less than 20 seconds. The heat treatment can be varied between 60-65° C.

Thus, in one embodiment, the second heat treatment of the present invention relates to heat treatment of less than 65° C., such as but not limited to less than 64° C., less than 63° C., less than 62° C., less than 61° C., less than 60° C., or even less than 55° C.

In another embodiment, the holding time is kept at less than 20 seconds, such as but not limited to less than 19 seconds, less than 18 seconds, less than 17 seconds, less than 16 seconds, less than 15 seconds, less than 14 seconds, less than 13 seconds, less than 12 seconds, less than 11 seconds, or less than 10 seconds.

In one embodiment, the BIO WPC 80 is heat treated at 63° C. for 15 sec. prior to spray drying.

Cooling

The BIO WPC preparation is optionally cooled to less than 15° C., to provide storage of the preparation.

Drying

The BIO WPC preparation of the present invention is optionally dried to become a dry powder composition, and the BIO WPC preparation can be dried by any drying means, which maintains the higher level of bioactive proteins.

In one embodiment, BIO WPC preparation of the present invention is dried by a spray dryer.

The temperature settings of the spray drier in the spray drying process are preferably adjusted in such a way that no thermal damage to the BIO WPC is done.

A spray dryer takes a liquid stream and separates the solute or suspension as a solid and the solvent into a vapor. The solid is usually collected in a drum or cyclone. The liquid input stream is sprayed through a nozzle into a hot vapor stream and vaporized. Solids form as moisture quickly leaves the droplets.

A nozzle is usually used to make the droplets as small as possible, maximizing heat transfer and the rate of water vaporization. Droplet sizes can range from 20 to 180 μm depending on the nozzle. There are two main types of nozzles: high pressure single fluid nozzle (50 to 300 bars) and two-fluid nozzles: one fluid is the liquid to dry and the second is compressed gas (generally air at 1 to 7 bars).

It will be appreciated that drying of the preparation can be carried out by any suitable means, in addition to spray-drying.

Ingredients retain their bioactive properties thanks to gentle, but effective heat treatment after evaporation Standardize for Large Scale Industrial processes have been shown to have adverse effects on the amount and activity of bioactive proteins in WPC products. For example, heat treatment during pasteurization and spray-drying significantly reduces the concentration and activity of LF, lysozyme, IgG, IgA, lactoperoxidase, and IGF-1.

Moreover, some special filtration processes remove the aggregates and higher molecular weight proteins to a considerable extent, including IGF-binding proteins, latent TGFβ2 complex, LF, and Igs.

Yet the present inventors here disclose that the mildly processed WPC of the present invention produced with less heat and without special filtration processes —yet still on an industrial processing scale, is not just a phenomena on in vitro level, but disclose significant in vivo motoric benefits, and thus a very useful protein source in formulas.

Special Proviso

Hydrolysates

Whey protein hydrolysates are the product of hydrolysis of whey proteins by proteolytic enzymes. The hydrolysates, which can be produced using a range of proteolytic enzymes, have improved functional properties including heat stability. However, whey protein hydrolysates do not maintain the desired bioactivity as the BIO WPC of the present invention.

High Heat Treatment

Heat treatment causes whey protein denaturation, which is an irreversible process. The mineral balance also changes during heat treatment. Calcium and phosphate becomes more insoluble and binds to the casein micellar structure.

This is reversible for temperatures below 100° C., thus subjecting e.g. the milk base of the sweet whey of the present invention to temperatures above 100° C. would generate whey proteins that would not be able to maintain the desired bioactivity as the BIO WPC of the present invention.

Radiation

Furthermore, it has long been known that the stability of proteins with respect to denaturation (as defined by aggregation) is lowered upon treatment with ionizing radiation, thus one advantage of the present invention is the improved bioactivity of the sweet BIO WPC compared to the conventional WPC. Thus, it may be advantageous to provide a milk base, wherein the milk base of the sweet whey has not been exposed to standard industrial processing steps selected from the group consisting of thermal processing, ultra-high temperature processing (UHT), hydrolysis and irradiation.

BIO WPC Preparations

The BIO WPC of the present invention seek to maintain the proteins in their native state whereby improvements in physiological effects are achieved, while large scale industrial production remains feasible.

At present, there is no standard of identity or compositional standards (e.g., minimum or maximum standards for protein content) for WPC. In many ways WPC are defined by the process by which they are obtained.

The production flow of bioactive WPC and conventional WPC products are shown in FIG. 7. A more detailed production diagram of BIO WPC is shown in FIG. 2.

Thus, in one embodiment, the present invention relates to a sweet whey preparation prepared/produced/manufactured by any of the method disclosed herein.

In another embodiment, the present invention relates to a sweet whey preparation, wherein the preparation is a powder. The powder is understood to comprise preferably less than 10%, more preferably less than 5% water. It is preferably a free flowing powder.

The WPCs are concentrates of whey having specified amounts of protein. Generally, WPC34 specifies a concentrate having not less than 34 percent protein, WPC50 specifies a concentrate having not less than 50 percent protein, WPC60 specifies a concentrate having not less than 60 percent protein, WPC75 specifies a concentrate having not less than 75 percent protein and WPC80 specifies a concentrate having not less than 80 percent protein.

These concentrates may be formed by ultrafiltration, recovery of the retentate, followed by concentration and spray drying of the retentate to form WPC34 and WPC50 powder; or e.g. diafiltration of the retentate, followed by concentration and spray drying to form WPC50, WPC60, WPC75 or WPC80.

In one embodiment, the BIO WPC is a BIO WPC80.

WPI is obtained by removing sufficient non-protein constituents from whey so that the finished dry product contains not less than 90 percent protein.

Thus, in one embodiment, the BIO WPC is further processed to a WPI with not less than 90 percent protein.

WPI is produced by membrane separation processes or ion exchange. In one example, fluid whey is subjected to microfiltration resulting in removal of lipids, diafiltration is then applied to form a permeate and whey protein isolate and the latter is then concentrated and spray dried to form WPI powder.

Lactoferrin Content

In a bioactive WPC, a measurably higher content of Lactoferrin is seen.

The levels of native lactoferrin were 3 times more in the BIO WPC than those in ConWPC measured by ELISA (Eurofins, Denmark) as seen in Table 1.

One embodiment of the present invention relates to a preparation comprising sweet whey, said sweet whey having being subjected to at least one heat treatment, wherein said heat treatment is less than 68° C. for less than 20 seconds, and wherein the said composition having a Lactoferrin content above 100 mg/l as measured by standard ELISA (Eurofins, Denmark).

Another embodiment of the present invention relates to a preparation obtainable by any process describe herein, wherein the said composition having a Lactoferrin content above 100 mg/l as measured by standard ELISA (Eurofins, Denmark).

Denaturation Level

The four major whey proteins represent 90% of all whey proteins. These are β-Lactoglobulin (β-Lg), α-Lactalbumin (α-La), Bovine Blood Serum Albumin (BSA) and Immunoglobulins (Ig's). The rate of denaturation is mainly controlled by heating temperature, heating time and pH but also protein concentration and ionic strength have been proved to have some effect.

Immunoglobulin's and BSA are the least stable whey proteins, β-Lg is intermediate and α-La is the most resistant protein to heat denaturation.

It is an objective of preferred embodiments of the present invention to keep proteins like these naturated as much as possible especially compared to conventional WPC, because the present inventors e.g. have realised that BIO WPC stimulates intestinal maturation both in preterm new-born pigs and in an intestinal cell model, and the general physical activity preterm new-born pigs.

In one embodiment, the present invention relates to a preparation comprising sweet whey, said sweet whey having being subjected to at least one heat treatment, wherein said heat treatment is less than 68° C. for less than 20 seconds, and wherein the sweet whey protein denaturation is 5% lower than the amount present in standard industrial produced sweet whey of the same origin [like WPC 80 (DI-8090) as produced by Example 3], such as but not limited to 10% lower, 15% lower, 20% lower, 25% lower, 30% lower, 35% lower or 50% lower.

IgG Content

In a bioactive WPC 80, a measurably higher content of IgG is seen.

The levels of native IgG were 1.3 times more in BIO WPC, than those in ConWPC measured by ELISA (Eurofins, Denmark).

One embodiment of the present invention relates to a preparation comprising sweet whey, said sweet whey having being subjected to at least one heat treatment, wherein said heat treatment is less than 68° C. for less than 20 seconds, and wherein the said composition having a IgG protein content above 5%.

Another embodiment of the present invention relates to a preparation obtainable by any process describe herein, wherein the levels of native IgG protein content is above 5%.

Another embodiment of the present invention relates to a preparation comprising sweet whey, said sweet whey having a native IgG level at least 1.1 times higher, than the level in a ConWPC as measured by ELISA with similar procedure (Eurofins, Denmark).

β-Lactoglobulin & CGMP Ratio

The BIO WPC of the present invention has a measurably higher content of β-Lactoglobulin, when compared to ConWPC, as shown in Example 4.

The aggregation of whey proteins is often assumed to be driven by β-Lactoglobulin due to its higher concentration than the other whey proteins in milk. Denaturation of β-Lactoglobulin, interactions of denatured β-Lactoglobulin with other whey proteins (α-La and BSA), and interactions of denatured β-Lactoglobulin with non-whey proteins (for example, κ-Csn) are important changes in milk during heating.

The dimer of β-Lactoglobulin dissociates between 30 and 55° C., but these changes are reversible and the monomers can rebound by cooling if the temperature does not exceed 60° C. When heating to temperatures above 60-70° C., the tertiary- and also partly secondary structure of the monomer starts to unfold, leading to expo-sure of the free thiol group (Cys121) and hydrophobic parts of the residues chain, resulting in a reactive monomer. The formation of these monomers is irreversible and they cannot refold to native state.

Thus, in one embodiment, the present invention relates to a preparation comprising sweet whey, said sweet whey having being subjected to at least one heat treatment, wherein said heat treatment is less than 68° C. for less than 20 seconds, and wherein the said composition having a Beta/CGMP ratio above 2.5.

Another embodiment relates to a preparation comprising sweet whey, said sweet whey having being subjected to at least one heat treatment, wherein said heat treatment is less than 68° C. for less than 20 seconds, and wherein the said composition having a content of β-Lactoglobulin higher than 33%.

Another embodiment of the present invention relates to a preparation obtainable by any process describe herein, wherein the said composition having a content of β-Lactoglobulin higher than 33%.

Caseino-Glyco-Macropeptide

A piglet study has confirmed that dietary sialic acid using CGMP as a source of sialic acid improves learning and memory during early development.

The BIO WPC of the present invention has a slightly higher level of CGMP, when compared to ConWPC, as shown in Example 4.

In one embodiment, the present invention relates to a preparation comprising elevated levels of the casein fragment caseino-glycomacropeptide (cGMP).

Another embodiment relates to a preparation comprising sweet whey, said sweet whey having being subjected to at least one heat treatment, wherein said heat treatment is less than 68° C. for less than 20 seconds, and wherein the said preparation having levels of the casein fragment caseino-glycomacropeptide (cGMP)/protein higher than 17.5%.

Another embodiment of the present invention relates to a preparation obtainable by any process describe herein, and wherein the said preparation having levels of the casein fragment caseino-glycomacropeptide (cGMP)/protein higher than 17.5%.

α-Lactalbumin

The BIO WPC of the present invention has a measurably higher content of α-lactalbumin, when compared to ConWPC, as shown in Example 4.

α-lactalbumin is the least heat resistant whey protein with a denaturation temperature around 62° C., but the unfolding at this temperature is reversible. It does not form aggregates or modified monomers at heating temperature below 80° C., at neutral pH (pH 6.6-6.8).

One embodiment relates to a preparation comprising sweet whey, said sweet whey having being subjected to at least one heat treatment, wherein said heat treatment is less than 68° C. for less than 20 seconds, and wherein the said preparation having a content of α-lactalbumin higher than 9%.

Another embodiment of the present invention relates to a preparation obtainable by any process describe herein, and wherein the said preparation having a content of α-lactalbum higher than 9%.

"Other Protein+Aggregates"

When calculating "other protein+aggregates" in the WPC, there is clearly a considerably lower content in the Bioactive WPC. A large part of these proteins in the normal WPC 80 would be Beta-Ig aggregates.

One embodiment relates to a preparation comprising sweet whey, said sweet whey having being subjected to at least one heat treatment, wherein said heat treatment is less than 68° C. for less than 20 seconds, and wherein the said preparation having a content of "other protein+aggregates" lower than 20%

Another embodiment of the present invention relates to a preparation obtainable by any process describe herein, and wherein the said preparation having a content of "other protein+aggregates" lower than 20%.

TGF-β2

BIO WPC contained 10 times more TGF-β2 than Con-WPC as shown in FIG. 8.

One embodiment relates to a preparation comprising sweet whey, said sweet whey having being subjected to at least one heat treatment, wherein said heat treatment is less than 68° C. for less than 20 seconds, and wherein the said preparation having a content of TGF-β2 higher than $2 \times 10^5$.

Another embodiment of the present invention relates to a preparation obtainable by any process describe herein, and wherein the said preparation having a content of TGF-β2 higher than $2 \times 10^5$.

BSA

By non-reducing SDS-PAGE, BSA levels were determined to be higher in BioWPC vs. ConWPC before and after aggregate removal (P<0.05, FIG. 7).

Improved Brain Function

Preterm infants show delayed development of motor function after birth. This may relate to functional immaturity of many organs, including the gut and brain. Using pigs as model for preterm infants—originally developed by the present inventors a generically described in Am J Physiol Regul Integr Comp Physiol 310: R481-R492, 2016 hereby incorporated by reference—the present inventors show that early initiation of enteral feeding with BIO WPC stimulates both gut growth and neonatal physical activity.

The present invention relates to the field of neuronal health and development. The invention specifically relates administration of sweet whey composition capable of promoting the establishment of cognitive function in infants, especially preterm, small for gestational age, low birth, very low and extremely low birth weight infants.

Preterm birth interrupts normal fetal growth with consequences for postnatal growth and organ development. In preterm infants, many physiological deficits adapt and disappear with advancing postnatal age, but some may persist into childhood. The present inventors hypothesized that preterm birth would induce impaired organ growth and function during the first postnatal week in pigs, while motor abilities and behavioral characteristics would show more persistent developmental delay.

Preterm pigs show delayed neonatal arousal and impaired physical activity, coordination, exploration, and learning, relative to term pigs (all P<0.05). Supplementation of parenteral nutrition during the first 5 days with an enteral milk diet did not affect later outcomes. The preterm pig is a relevant animal model to study early dietary and interventions that support postnatal maturation and neurodevelopment in preterm infants.

The present inventors compare the effects of a mildly-heat-treated WPC (Bioactive WPC, Arla Foods Ingredients, AFI) with a conventionally-heat-treated WPC and studied the difference in physical activity.

Physical activity can be monitored in and open field test, which is an experiment used to assay general locomotor activity levels.

The BioWPC intervention increased physical activity and locomotion in preterm pigs, and this is due to direct beneficial effects on early brain development. Thus, in one embodiment, the present invention relates to a bioactive WPC for promoting the establishment of healthy and normal cognitive function in young mammals.

The bioactive WPC according to the invention may be used for promoting the healthy establishment of cognitive function and/or prevention of, or repair of, or reduction in the severity of cognitive function impairment in a young mammal.

It may further be used for treatment of disorders associated with the delayed establishment of cognitive function or cognitive function impairment in a young mammal.

The disorders may be any one or more of the following: delayed and/or impaired learning ability, loss of, or poor development of executive functions, higher reasoning impairment, memory impairment, delay in language development, learning disabilities, abnormally poor concentration including Attention Deficit Hyperactivity Disorder (ADHD), abnormally decreased intelligence, abnormally poor mental performance, mood disturbance, or autism.

Humans or animals and, in particular, a fetus, pre-term or term born infant, toddler or child or a young adult up to the age of twenty years old may benefit from the invention.

The invention may be especially beneficial to those infants having experienced intrauterine growth retardation (IUGR), or having a low, very low or extremely low birth weight, being small for gestational age, having suffered hypoxemia-ischemia at birth, postnatal complications, postnatal steroid treatments or any other adverse event in the post-natal period, and/or suffering from cognitive function impairment, such as impaired learning and memory, lack of curiosity, poor attention span and thus, poor mental performance, central nervous system growth retardation, either in utero, or, during or after birth.

Physical activity was recorded by continuous video surveillance using infrared cameras installed over each incubator and connected to an HD recorder with built-in motion detection. The digital output for each camera allowed recording of the status of the individual piglets as being either active or resting.

With the PIGLWin application (Ellegaard Systems, Faaborg Denmark), the proportion of active time was automatically registered for every hour. The cameras were turned off during any handling and contact with the pigs.

Activity recording was performed from total enteral feeding commenced on day 3 at 9:00 am and ended just before pigs were euthanized on day 5 at 9:00 am.

The proportion of active time was analyzed from means of recordings covering the day and night time, respectively.

On day 4, spontaneous motor activity was evaluated in an open field arena (1.20×1.20 m), with a video camera mounted from the ceiling (bird's eye view) during a 3-min recording period. From these recordings, piglet movements were tracked and analyzed using a commercially available software (EthoVision XT10, Noldus Information Technology, Wageningen, The Netherlands) providing information on distance travelled inside the arena. Pigs that were clinically ill on day 4 were excluded from the test.

Initially, home cage activity was similar between groups (FIG. 18), but from late day 3 and onwards, the activity level was higher in the Bio group compared to the Con group (P=0.09), and significantly increased during the last half day prior to the euthanasia (P<0.05, FIG. 18). Further, in the open field test on day 4, Bio pigs walked almost twice the distance as that of the Con pigs (P<0.05, FIG. 4), overall supporting an increased motor activity in Bio pigs.

Result

BioWPC did not affect body and intestinal weights but significantly improved feeding tolerance compared with control pigs (P<0.01). BioWPC pigs also tended to show higher hexose absorptive capacity (P=0.09) and lower gut permeability (P=0.07).

BioWPC increased the villus height to crypt depth ratio, and proximal intestinal lactase activity (P<0.05). The time for acquisition of basic motor skills was similar between groups. The distance travelled in the open field arena was consistently longer in the BioWPC group, relative to controls (n=8, p<0.05).

Open-Field Arena (EthoVision XT10 Analysis)

Physical activity was recorded by continuous video surveillance using infrared cameras installed over each incubator and connected to an HD recorder with built-in motion detection. The digital output for each camera allowed recording of the status of the individual piglets as being either active or resting. With the PIGLWin application (Ellegaard Systems, Faaborg Denmark), the proportion of active time was automatically registered for every hour. The cameras were turned off during any handling and contact with the pigs. Activity recording was performed from total enteral feeding commenced on day 3 at 9:00 am and ended just before pigs were euthanized on day 5 at 9:00 am. The proportion of active time was analyzed from means of recordings covering the day and night time, respectively.

On day 4, spontaneous motor activity was evaluated in an open field arena (1.20×1.20 m), with a video camera mounted from the ceiling (bird's eye view) during a 3-min recording period. From these recordings, piglet movements were tracked and analyzed using a commercially available software (EthoVision XT10, Noldus Information Technology, Wageningen, The Netherlands) providing information on distance travelled inside the arena. Pigs that were clinically ill on day 4 were excluded from the test.

In one embodiment, the present invention relates to a preparation comprising sweet whey, wherein the bioactivity of the proteins in said sweet whey are preserved by reduced thermal processing in industrial settings characterized in preterm pigs delivered from sows by caesarean section at 105 d gestation having an motor activity (as evaluated in an open field arena (1.20×1.20 m) with a video camera mounted from the ceiling (bird's eye view) during a 3-min recording period) with the following constraint:

walking distance in cm above 600 on day 4.

In the present context, a walking distance in cm above 600 on day 4 relates to improved walking distances compared to conventional WPC preparations, and thus the aim is to have walking distances measurements on day 4 significantly over the observed level in preterms pigs. In the settings tested herein, walking distances over about 400 to 500 cm may already be indicative of improvements.

In one embodiment, then a threshold of above 600 cm on day 4 shows a clear significant improvement of the motoric function in the pig model, and thus the present invention relates to walking distance above 600 cm on day 4, such as but not limited to 600 cm on day 4, 650 cm on day 4, 700 cm on day 4, 750 cm on day 4, 800 cm on day 4, 850 cm on day 4, 900 cm on day 4, 950 cm on day 4, 1000 cm on day 4, 1100 cm on day 4 or more.

PIGLWin Application

PIGLWin application is a video surveillance and activity detection system designed and made for the preterm pig model by Ellegaard Systems A/S, Denmark. The system consists of 20 mini-cameras with IR-light mounted over each pig's incubator and running during the study 24/7. Active time, resting time, and number of active episodes can be extracted from the system and used for reach on animal activities.

Withheld Feeding

Feeding intolerance was defined as feed-reduction or complete with-holding of feed at any time point for any reason. The decision to reduce or with-hold feeding (at each feeding time point), was based on a clinical assessment including the following criteria: signs of pain or discomfort, vomit, abdominal distension, bloody stools.

The incidence of feeding intolerance was calculated as the number of pigs in each group experiencing feed-reduction, divided by group size.

On this background, there was an incidence of 44% in ConWPC and 0% in BioWPC.

Thus, in one embodiment the present invention relates to a preparation for use in reducing the feeding intolerance in an infant/preterm infant.

Medicament

Whey proteins have been applied in several medicaments such as attenuating a reduction in muscle function, osteoblast growth, etc., and thus another important embodiment relates to a preparation of bioactive WPC according to the present invention for use as a medicament.

Preterm Infant Preparations

Preterm infants are a high-risk patient population with a variety of developmental complications, including delayed neurodevelopment and a high incidence of brain insults. Even when newborn preterm infants show no clinically observable brain defects, it is common to observe that such infants exhibit slower postnatal development of motor skills, compared with term infants. Even at term-corrected age, the brains in preterm infants may show compromised gray matter volume and altered developmental trajectory, probably explaining delayed neonatal arousal and immature neuromuscular function and brain electroencephalography.

In more longterm studies, preterm infants have shown reduced postural complexity and lowered motor function, potentially persisting until school age, or even into adulthood.

Thus, early impairment of physical locomotion in preterm infants may have long-term consequences.

In one embodiment, the present invention relates to a preparation for use in accelerating brain development in an infant/preterm infant.

Another embodiment, relates to a preparation according to the present invention for use in promoting motoric skills in an infant/preterm infant.

The present invention is applicable in preparations which purports to be or is represented for special dietary use solely as a food for infants by reason of its simulation of human milk or its suitability as a complete or partial substitute for human milk.

Thus, one embodiment of the present invention relates to an infant formula comprising a preparation as described herein.

In the present context, then the term "Infant formula" relates to the Commission Directives 2006/141/EC of 22 Dec. 2006 and/or 91/321/EEC of 14 May 1991 wording on infant formulae and follow-on formulae, article 1.2 (c), the term "infant formula" means foodstuffs intended for particular nutritional use by infants during the first four to six months of life and satisfying by themselves the nutritional requirements of this category of persons.

It has to be understood that infants can be fed solely with infant formulas, or that the infant formula can be used by the carer as a complement of human milk. It is synonymous to the widely used expression "starter formula".

The present invention also relates to "Follow-on formulae": according to the Commission Directives 2006/141/EC of 22 Dec. 2006 and/or 91/321/EEC of 14 May 1991 on infant formulae and follow-on formulae, article 1.2 (d), the term "follow-on formulae" means foodstuffs intended for particular nutritional use by infants aged over four months and constituting the principal liquid element in a progressively diversified diet of this category of persons.

Thus, in one embodiment, the present invention disclose a follow on formula comprising a preparation according to the invention.

The present invention also relates to "Growing-up milk": milk-based nutritional composition especially adapted to a child of between one year and three years old.

The present invention also relates to "Human Milk fortifier": Nutritional composition for infants or young children intended to be added to or diluted with human milk.

Administration of BIO WPC Infant Formulas

The administration of the bioactive preparation according to the present invention may be to a foetus via the mother.

It may also be to a pre-term or term-born infant either directly or via mothers' milk.

The administration may be also be to a child or young adult, generally up to the age of twenty years old, or the equivalent age in an animal.

The BIO WPC preparations of the present invention may be administered directly to the infant or young child in its pure form, or diluted in water or breast milk, in a food supplement, or together with in a milk fortifier, or any milk support used during trophic feeding, in an infant formula, or in a milk based drink.

The BIO WPC preparations of the present invention is typically administered to the infant, or young child as a daily dose of 30 to 80%, preferably 60% w/w, of the total protein intake.

The administration period for the foetus is generally at least one week, preferably two weeks, more preferably at least one month, and the administration period for the infant or young child is generally at least 4 weeks, preferably 2-12 months, and more preferably at least 18 months and even more preferably up until the child is in the early adulthood (20 years old).

The BIO WPC preparations of the present invention may be administered to pre-term or term-born infant, or child or young adult as a dose of 1.6-3.2 g protein/100 kca, preferably, 1.6-2.2 g protein/100 kca, and more preferably 1.8-2.1 g protein/100 kcal.

In one embodiment the BIO WPC or preparations of the present invention is administered to the infant as a dose of 1.0 to less than 1.6 g protein/100 kcal.

The invention relates to a composition comprising 30-80%, preferably 60% BIO WPC preparations of the present invention, for healthy establishment and development of cognitive function throughout the young life of the child until adolescence or even until age twenty. In particular, it relates to a composition for the prevention/reduction of the severity of disorders such as impaired learning ability, loss of, or abnormally poor higher reasoning, abnormally poor concentration including ADHD, delay in language development, memory and executive function problems, abnormally low intelligence, and thus, abnormally low mental performance and autism in a young mammal.

The invention may be particularly useful for those young mammals who are born prematurely or who have suffered from IUGR.

General

It should be understood that any feature and/or aspect discussed above in connections with the preparations according to the invention apply by analogy to the methods and uses described herein.

The terms bioactive whey, BIO WPC preparations and BIO WPC, are used interchangeably.

The following figures and examples are provided below to illustrate the present invention. They are intended to be illustrative and are not to be construed as limiting in any way.

Tables

TABLE 1

Macronutrient compositions and levels of lactoferrin and IgG

| | Bio | Con |
|---|---|---|
| Energy (kJ/l) | 4495 | 4504 |
| Protein (g/l) | 79 | 79 |
| Lactoferrin (mg/l) | 264.6 | 88.4 |
| IgG (g/l) | 5.2 | 4.0 |
| Carbohydrate (g/l) | 62 | 62 |
| Lactose (g/l) | 47 | 47 |
| Maltodextrin (g/l) | 15 | 15 |
| Fat (g/l) | 57 | 57 |

The macronutrients compositions of the formulas were calculated based on the product specification provided by the manufactories. Bio, formula containing bioactive WPC; Con, formula containing conventional WPC; IgG, immunoglobulin G

TABLE 2

A composition of Acid Whey

| | | Acid Whey (80 CV200) |
|---|---|---|
| Total Solid | [%] | 94.5 |
| Protein | [%] | 78 |
| Lactose | [%] | 7.4 |
| Galactose | [%] | N.A |
| Fat | [%] | 4.5 |
| Ash | [%] | 4.2 |
| Calcium | [%] | 0.25 |
| Phosphate | [%] | 0.353 |
| Magnesium | [%] | 0.0202 |
| Sodium | [%] | 1.224 |
| Potasium | [%] | 0.12 |
| Cloride | [%] | 0.43 |
| pH | | 7.5 |
| Alpha-La | [%] | 10.2 |
| Beta-Lg | [%] | 37.1 |
| GMP | [%] | 0 |
| SUM WP | | 47.3 |
| IgG | [%] | N.A |
| Lactoferrin | [%] | 1.7 |
| a-la/protein | | 13.1% |
| B-lg/Protein | | 47.6% |
| cGMP/Protein | | 0.0% |
| IgG/Protein | | N.A. |
| Lactoferrin/Protein | | 2.2% |

TABLE 2-continued

A composition of Acid Whey

| | Acid Whey (80 CV200) |
|---|---|
| Other Protein + Denatured | 37.2% |
| PROT/TS (WPC) | 82.5% |

Figure 1:
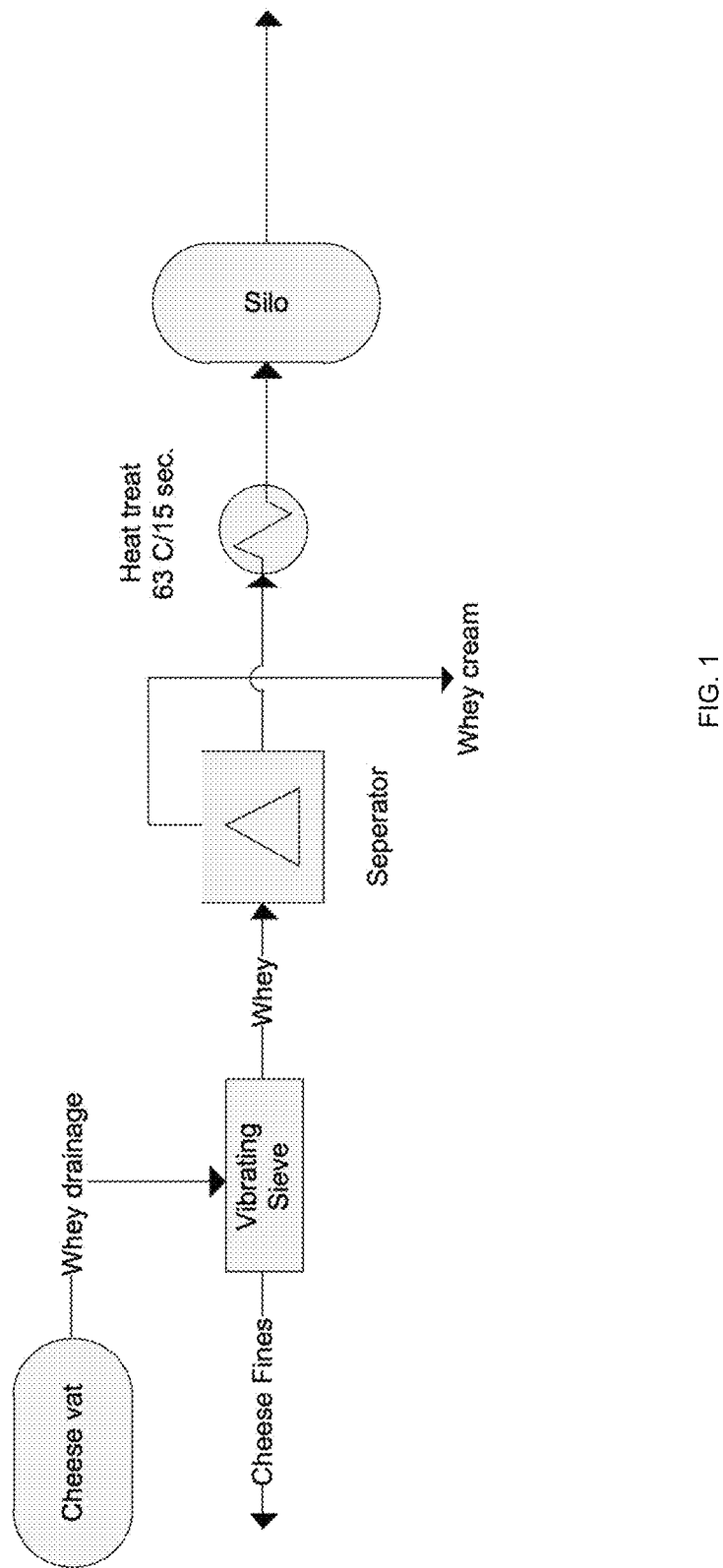
FIG. 1
Figure 2:
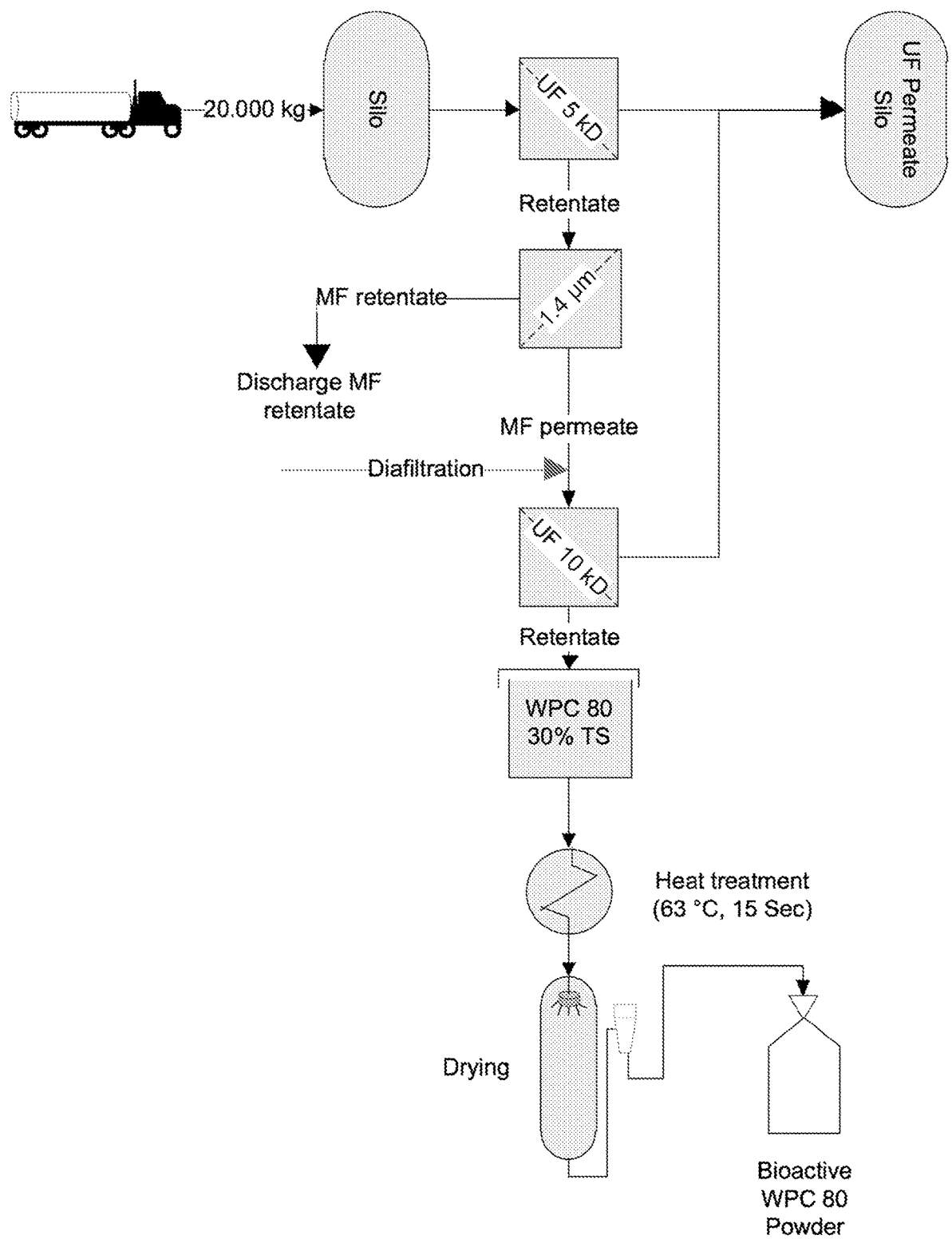
Figure 3:
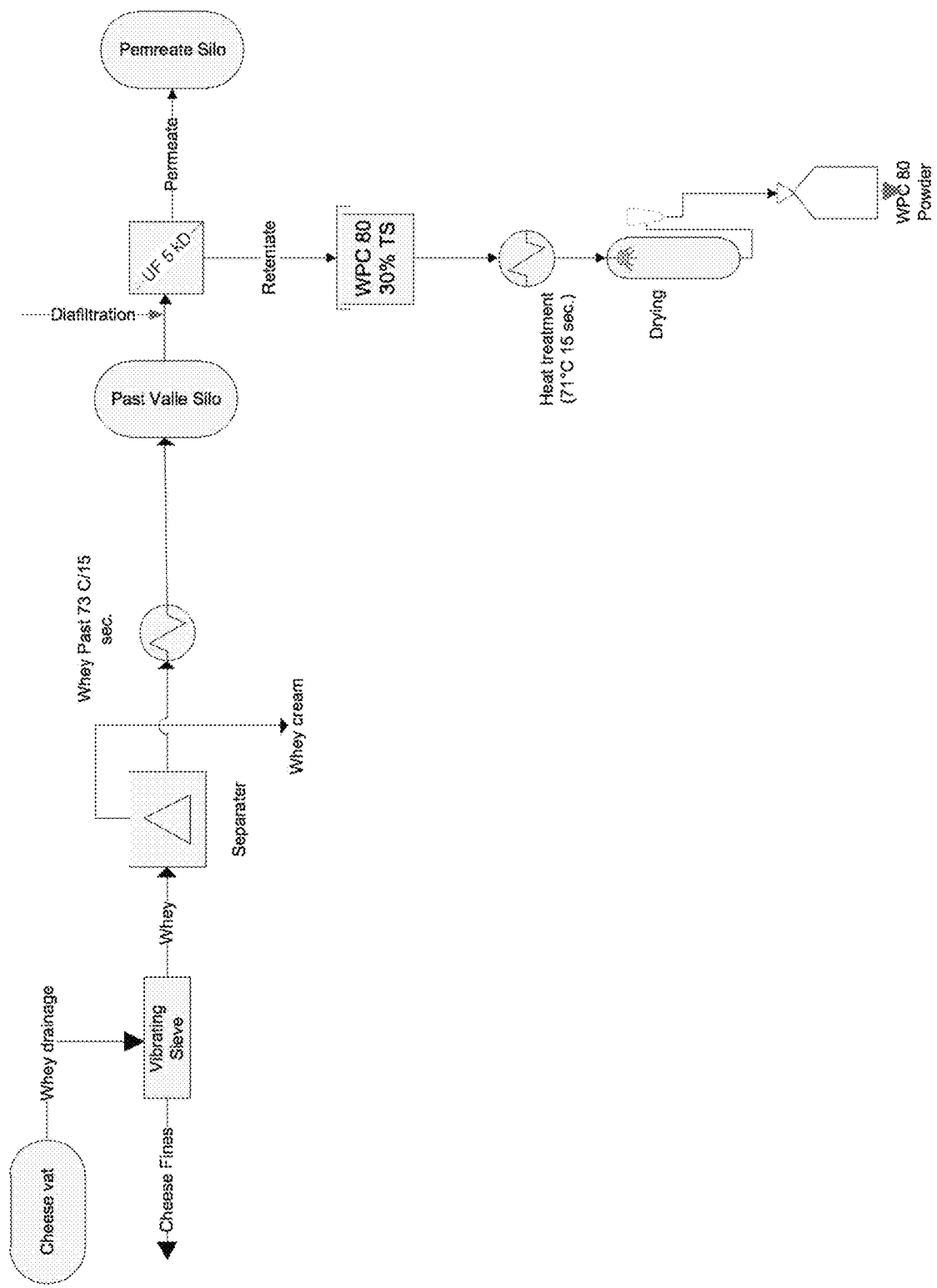

Whey drainage and processing at the cheese plant for Bioactive WPC.

FIG. 2

Bioactive WPC production diagram.

FIG. 3

Standard WPC 80 production diagram.

FIG. 4

Open field assessment scores of locomotion (distance travelled within 3 min sessions) in BioWPC (N=8) and ConWPC (N=8) group. Data are mean±SEM. P<0.05. Walking distance in open field test on day 4. Values are means+ SEM. Values indicated by '*' differ between each other, P<0.05. Bio, formula containing bioactive WPC; Con, formula containing conventional WPC.

FIG. 5

Schematic diagram displaying the production flow of bioactive WPC and conventional WPC. BioWPC, bioactive WPC; Bio, BioWPC containing formula; Con, ConWPC containing formula; ConWPC, conventional WPC; WPC, whey protein concentrate.

FIG. 6

Protein composition in BioWPC and ConWPC with and without aggregate removal by centrifugation analysed by SDS-PAGE.

FIG. 7

Relative quantification of protein band volume for LF, BSA, β-Lg and α-La. Values (means±SEM, n=3 for triplicates of sample preparation) indicated by '*' differ between each other, P<0.05. BioWPC, bioactive WPC; ConWPC, conventional WPC; β-lg, β-lactoglobulin; α-La, α-lactalbumin; BSA, bovine serum albumin; LF, lactoferrin.

FIG. 8

Western-blotting analysis of TGF-β2 in the two WPCs (triplicates) with and without removal of aggregates by centrifugation. The relative abundance of TGF-β2 is presented as means±SEMs. Values indicated by '*' differ between each other, P<0.05. BioWPC, bioactive WPC; ConWPC, conventional WPC.

FIG. 9

Effects of BioWPC and ConWPC on the cell cytotoxicity (A) and proliferation (B) of IPEC-J2 cells in vitro. Values are means±SEM, n=3 representing triplicates in three different cell passages. Values indicated by '*' differ between each other, P<0.05. Means without a common letter differ, P, 0.05. BioWPC, bioactive WPC; ConWPC, conventional WPC; CON, negative control in the proliferation assay.

FIG. 10

Intestinal digestive and absorptive functions and permeability. Plasma galactose levels at 20 min after administration of oral boluses of galactose solution on day 3 and at 40 min after administration of oral boluses of lactose solution.

FIG. 11

Intestinal permeability presented as measured by the urinary lactulose to mannitol ratio (L/M ratio) after oral administration of lactulose/mannitol solution.

FIG. 12

Brush border enzyme activity in the proximal region of small intestine. Values are means±SEM. Values indicated by '*' differ between each other, P<0.05. Bio, formula containing bioactive WPC; Con, formula containing conventional WPC

FIG. 13

Villous height and crypt depth in the proximal small intestinal region.

FIG. 14

General physical activity. Trend of proportion of active time during postnatal day 3 and 4 showing in every half day.

EXAMPLES

Example 1—Manufacturing of Bioactive WPC

Bioactive WPC is produced from whey drainage from cheese production. After whey drainage, cheese fines are removed and whey cream is also removed in a continues centrifugal separator.

Heat treatment between 60-68° C. is performed in order to reduce cheese starter culture bacterial growth and preventing further pH drop in the whey. The whey is cooled to below 5° C. and stored in a silo tank before further processing preferably less than 2 days.

The whey is concentrated into WPC 35 using a 5 or 10 Kd UF Spiral Wound membrane. The temperature is kept in the range of 5-18° C.

The feed pressure is in the range of 0.5-3.5 bar and a pressure drop per element ranging from 0.5 bar to 1.3 bar.

A second filtration reduces the bacterial count in the WPC 35. The bacterial reduction is performed using a Ceramic Membrane with a pore size ranging from 0.5 μm to 2.0 μm. The temperature is kept at 5-18° C. and the Trans Membrane Pressure (TMP) should be between 0.1 and 2.5 bar. The VCF is in the range of 2-100.

Permeate from the ceramic filtration is further processed into WPC 80 using a 5 or 10 Kd UF Spiral Wound membrane. The temperature is kept in the range of 5-18° C.

The feed pressure is in the range of 0.5-3.5 bar and a pressure drop per element ranging from 0.5 bar to 1.3 bar. An SW membrane that can be sanitized at temperatures above 70° C. is preferable in order to keep the high microbial status after MF filtration.

The WPC 80 is heat treated at 63° C. for 15 sec. prior to spray drying.

Example 2—Manufacturing of Bioactive WPC80

Bioactive WPC 80 is produced using whey drainage from Tistrup Dairy, which produces Gouda cheese.

After whey drainage, cheese fines are removed in a Sweco vibrating sieve and whey cream is removed in a continues centrifugal separator.

The whey is heat treated at 63° C. for 15 sec. to reduce cheese starter culture bacterial growth and preventing further pH drop in the whey.

The whey is cooled to below 5° C. and stored in a silo tank.

20,000 kg whey is concentrated into WPC 35 using a 5 Kd KOCH HKS 328 UF Spiral Wound membrane. The temperature is 10° C. The feed pressure is 3.0 bar and the pressure drop per membrane element is 1.0 bar.

The second filtration reduces the bacterial count in the WPC 35 retentate. A ceramic Tami 1.4 μm isoflux membrane is used. The filtration is performed at 15° C. and the TMP is 1.5 bar. The VCF is set to 50.

Permeate from the ceramic filtration is further processed into WPC 80 using a 10 Kd KOCH hpht 131 UF Spiral Wound membrane. Before filtration, plant and membranes are sanitized at 70° C. just before filtration. During the production, the temperature is 10° C. The feed pressure is 3.0 bar and the pressure drop per membrane element is 1.0 bar.

The Bioactive WPC 80 retentate is heat treated at 63° C. for 15 sec. prior to spray drying.

Example 3—Manufacturing of Standard WPC 80

A standard WPC 80 is produced using whey drainage from yellow cheese production. After whey drainage, cheese fines are removed and whey cream is removed in a centrifugal separator.

Pasteurization at 73° C. for 15 sec. is performed to inactivate cheese starter culture and prevent further pH drop in the whey.

The whey is cooled and stored in a silo tank before further processing.

WPC 80 is produced using a 5 kD Koch HKS 328 membrane. The temperature is 10° C., the feed pressure is 3.0 bar and there is a pressure drop per membrane element at 1.0 bar.

The WPC is heat treated at 71° C. for 15 sec. prior to spray drying.

Example 4—Composition of Bioactive WPC 80 and WPC 80

The present inventors compare mildly-heat-treated WPC (Bioactive WPC, Arla Foods Ingredients, AFI) with a conventionally-heat-treated WPC (Lacprodan DI-8090, AFI)

| | | Powder | |
| --- | --- | --- | --- |
| | | Bioactive WPC 80 | WPC 80 (DI-8090) |
| Total Solid | [%] | 95.36 | 93.96 |
| Protein | [%] | 79.35 | 75.6 |
| Lactose | [%] | N.A. | 4.42 |
| Galactose | [%] | 0.28 | 0.76 |
| Fat | [%] | 5.52 | 6.89 |
| Ash | [%] | 2.79 | 2.67 |
| Calcium | [%] | 0.417 | 0.372 |
| Phosphate | [%] | 0.302 | 0.3075 |
| Magnesium | [%] | 0.0726 | 0.0563 |
| Sodium | [%] | 0.156 | 0.205 |
| Potassium | [%] | 0.611 | 0.5425 |
| Chloride | [%] | 0.04 | 0.08 |
| pH | | 6.52 | 6.44 |
| Alpha -La | [%] | 10.86 | 8.90 |
| Beta-Lg | [%] | 38.91 | 31.71 |
| GMP | [%] | 14.16 | 13.14 |
| IgG | [%] | 5.30 | 3.80 |
| Lactoferrin | [%] | 0.270 | 0.085 |
| a-la/protein | [%] | 13.7 | 11.8 |
| B-lg/protein | [%] | 49.0 | 41.9 |
| cGMP/protein | [%] | 17.9 | 17.4 |
| IgG/protein | [%] | 6.7 | 5.0 |

-continued

|  |  | Powder | |
| --- | --- | --- | --- |
|  |  | Bioactive WPC 80 | WPC 80 (DI-8090) |
| Lactoferrin/protein | [%] | 0.3 | 0.1 |
| Other protein + denatured | [%] | 12.4 | 23.8 |
| PROT/TS (WPC) | [%] | 83.2 | 80.5 |
| Beta:CGMP | [%] | 2.75 | 2.41 |

Example 5—Settings in Preterm Neonates Piglet Model

Preterm term infants suffer from impaired growth and brain development postnatally. Early enteral feeding with high quality formula plays an important role to stimulate growth and organ maturation, which may be important for long-term neurodevelopment.

Here we investigate the effects of gentle treatment of WPC on physical activity and motoric control in preterm pigs.

Materials and Methods

Pigs, Nutrition Protocol, and General Experimental Design

Nighty-two preterm pigs were delivered from four sows by caesarean section at 105-106 d gestation (Large White× Danish Landrace×Duroc, Askelygaard Farm, Roskilde, Denmark; term=116±2 days). Oro-gastric feeding tube (6 F, Portex, Smiths Medical, St Paul, MN, USA) was placed into the stomach for enteral nutrition (EN), and vascular catheter (4 F, Portex) was inserted in the umbilical artery for parental nutrition (PN).

Pigs were reared in temperature-regulated individual incubators with oxygen supply and given 16 ml/kg maternal serum during the first 24 h after birth to achieve passive immunological protection. All pigs received parenteral nutrition (PN) for the first 2 days as previously described (ref.). Pigs also received their respective milk diets as minimal enteral nutrition (MEN; 24-40 ml/kg/d) for the first two days and as full enteral nutrition (120 ml/kg/d) from day 3 to euthanasia.

The studies were approved by the National Committee on Animal Experimentation in Denmark.

Pigs Selected for BIO WPC Protocol

Thirty one caesarean-delivered preterm pigs were assigned into two groups fed formula with gentle treatment of WPC (BioWPC, n=15) or conventional WPC treatment (ConWPC, n=16).

Feeding

The two milk formulas were made by mixing the following ingredients and contained similar macronutrient compositions and energy level (Table 1): BioWPC, and ConWPC, Arla Foods Ingredients, AFI, Viby J. Denmark); lactose (Variolac 960, AFI); maltodextrin (Ross Polycose; Abbott Nutrition, Columbus, USA); lipids (Liquigen and Calogen; Nutricia, Allerød, Denmark) and vitamins and minerals (SHS Seravit; Nutricia).

After five days of feeding, organ weights, gut functions and incidence of necrotizing enterocolitis (NEC) were evaluated. Time for acquisition of basic motor skills (i.e. first opening of eyes, first stand, first walk) was noted and physical activity was recorded by cameras and analyzed (PIGLWin application). Motoric skills were further investigated by measuring the distance travelled in an open-field arena (EthoVision XT10 analyses).

Clinical Evaluation and Sample Collection

Pigs were continually monitored and killed if clinical symptoms of NEC such as abdominal distension, lethargy, cyanosis or bloody diarrhea were observed. All remaining pigs were euthanized for tissue collection on day 5.

Feeding intolerance was defined as withholding or reducing the amount of planned enteral feeding due to vomiting or abdominal distension.

After anaesthesia (Zoletil 50, zolazepam/tiletamin; Boehringer Ingelheim, Copenhagen, Denmark), cardiac blood was collected into heparin- or EDTA-containing tubes, and subsequently pigs were euthanized with an intracardiac injection of pentobarbitone sodium (60 mg/kg).

Individual weights of the heart, lungs, liver, kidneys, spleen, stomach, small intestine and colon were recorded.

The length of the small intestine was recorded in a relaxed stage. The whole small intestine was divided into three sections of equal length, proximal (Prox), middle (Mid) and distal (Dist). Whole-wall tissue samples were taken at the middle of each region, and immediately snap-frozen in liquid nitrogen, and stored at −80° C. for further analyses. Whole-wall tissue samples were also taken from each region at the same position, and were immediately submerged into paraformaldehyde solution. A one-centimeter segment of Dist tissue from 10 cm prior to ileocecal junction and of colon tissue from the apex region was fixated in Clarke's solution for later goblet cell quantification.

The mucosal lesions in the stomach, Prox, Mid, Dist, and colon were evaluated macroscopically and a lesion score was assigned to each region.

The score was graded according to following criteria: 1 no or minimal focal hyperaemic gastroenterocolitis; 2 mild focal gastroenterocolitis; 3 moderate locally extensive gastroenterocolitis; 4 severe focal gastroenterocolitis; 5 severe locally extensive hemorrhagic and necrotic gastroenterocolitis; or 6 severe extensive hemorrhagic and necrotic gastroenterocolitis.

Pigs with a score of three or above in any of the Prox, Mid, Dist and Colon regions, was diagnosed as NEC. The severity of inflammation in stomach and intestine was reflected by the mean of the lesion scores in stomach, colon, and the mean of the average lesion scores in Prox, Mid, Dist.

Statistical Analysis

Levels of proteins in WPCs were analyzed by student t-test (GraphPad Prism 5.0, La Jolla, CA, USA).

Data of cell cytotoxicity and cell proliferation were analyzed by a linear mixed model with treatment and cell passage as fixed factors followed by post hoc Tukey test (JMP, SAS Institute, Cary, USA). Binary data such as NEC incidence were evaluated using logistic regression in R (version 3.1.1). NEC lesion scores were analyzed using non-parametric analysis with the nparcomp package.

Continuous outcomes were compared among groups using general linear model with adjustments, e.g. sow, sex, birth weight. Repeated measurement of daily physical activity was analyzed using the lmer function for mixed modeling as repeated measures and comparisons were made with the lsmeans package.

To confirm validity of modeled data, residuals and fitted values were assessed for normality and variance homogeneity, which for some outcomes required log-transformation of data before modeling. Resulting P-values were evaluated at a 5% significance level. The multcomp single-step method was used to adjust P values for multiple comparisons within each outcome measure and point of measurements.

Data are presented as raw arithmetic mean and SEM, unless otherwise stated.

Figure 7:
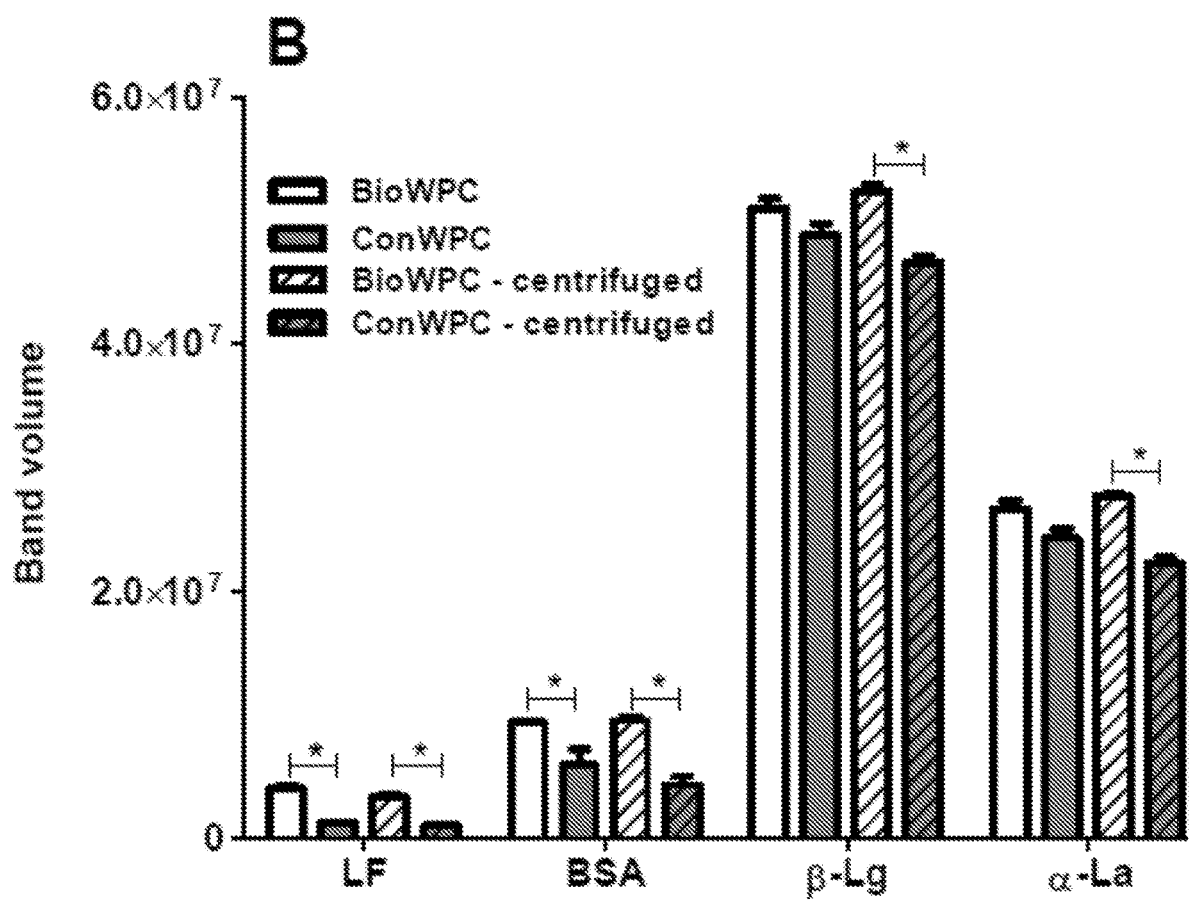

Example 6—Whey Protein Concentrate Products and Analysis of Bioactive Markers ConWPC and BioWPC used in experiments were manufactured at AFI from sweet whey by similar processing procedures with differences only in the number of pasteurization steps and temperature of spray-drying (FIG. 7).

Protein aggregation, protein compositions before and after removal of aggregates, and levels of LF, IgG, IGF-I, and TGF-β2 were measured as the indicators of bioactivity.

The level of total protein was measured by BCA protein assay (Thermo Scientific) before and after removal of the aggregated protein (centrifuged at 15000×g, 4° C. for 30 min). WPCs before and after centrifugation (15 µg protein in each sample) were loaded in 15% SDS-PAGE gel in non-reducing conditions for major protein analysis. LF and IgG were also analyzed by Eurofines.

TGF-β2 was analyzed by Western blot using TGF-β2 antibody (Sc-90, Santa Cruz Biotechnology, CA, USA).

Aggregated protein in BioWPC was negligible, whereas approximate 20% protein was aggregated in ConWPC.

The levels of native LF and IgG measured by Eurofines were 3 and 1.3 times more in BioWPC than those in ConWPC (Table 1).

By non-reducing SDS-PAGE, LF and BSA levels were higher in BioWPC vs. ConWPC for both samples before and after aggregate removal (P<0.05, FIG. 7).

After aggregate removal, BioWPC also had higher levels of β-Lg and α-La than ConWPC (P<0.05, FIG. 7).

Figure 8:
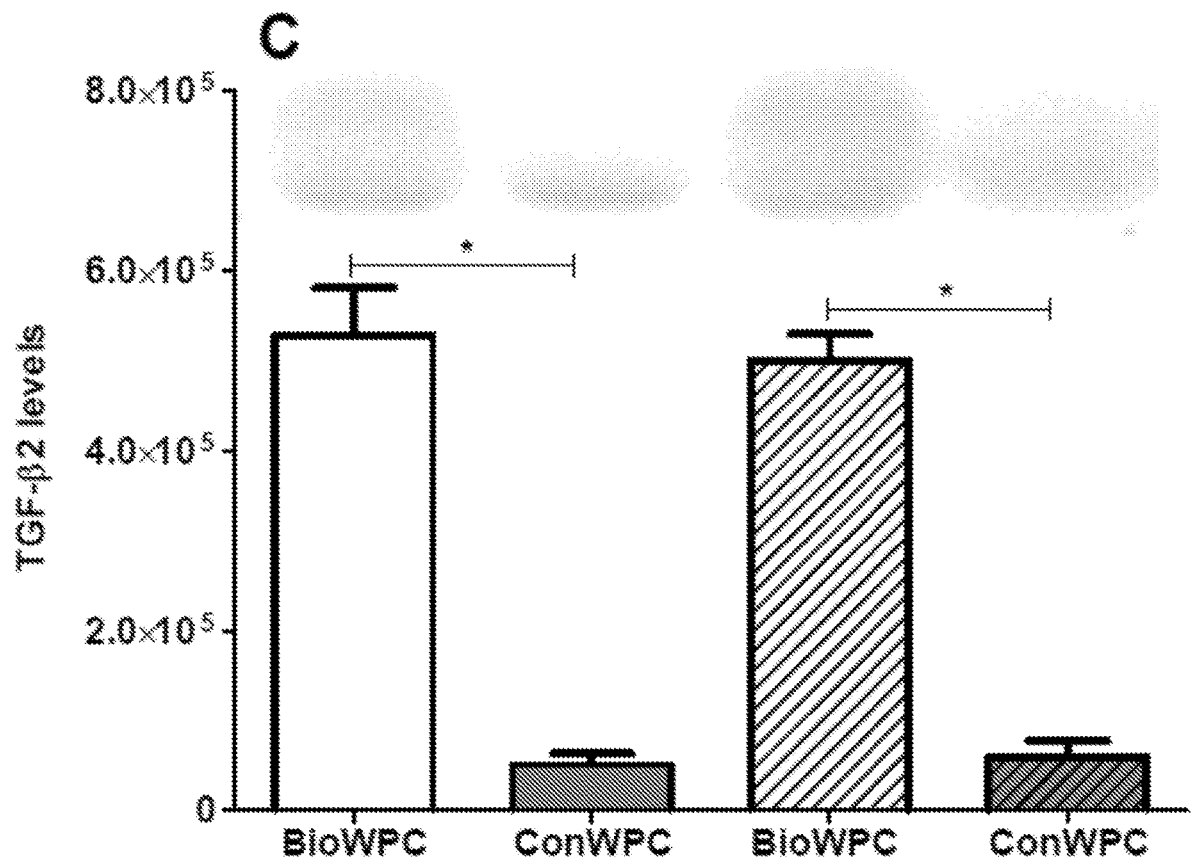
Figure 9:
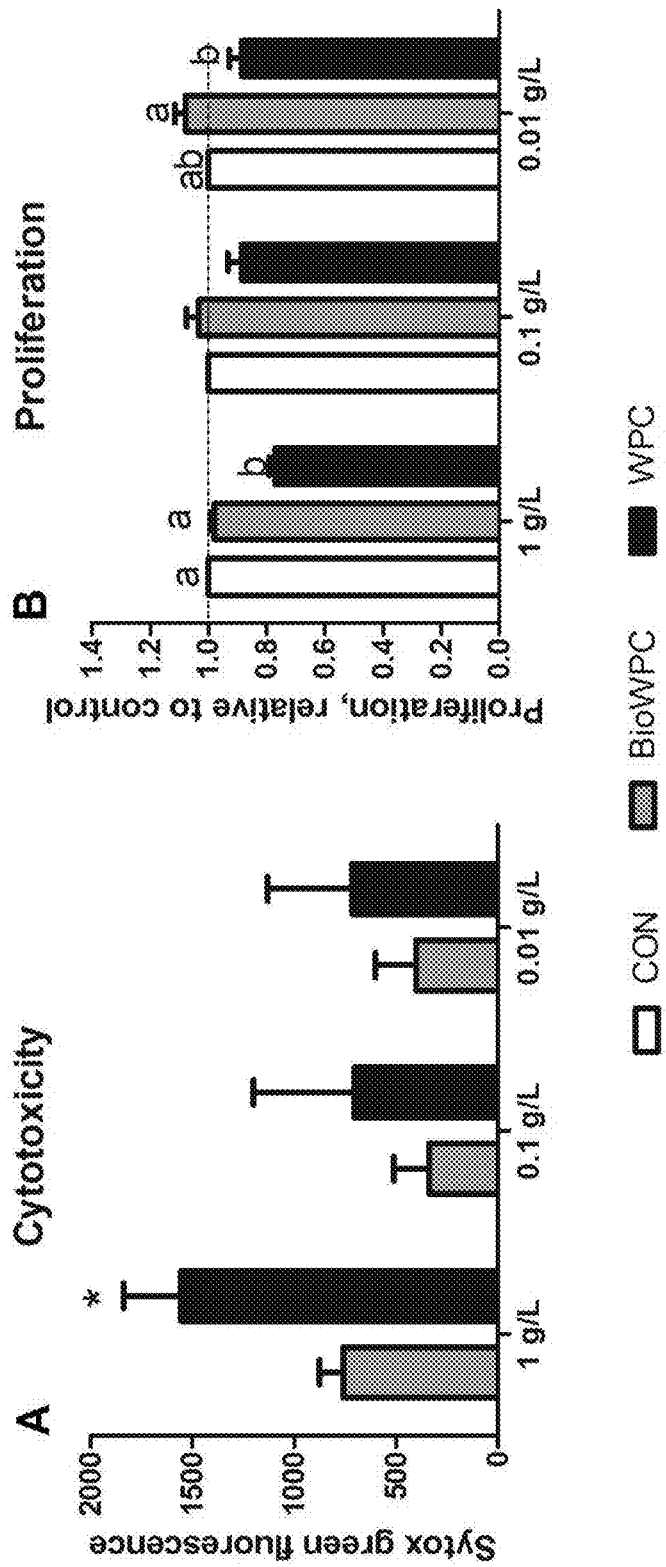
Figure 10:
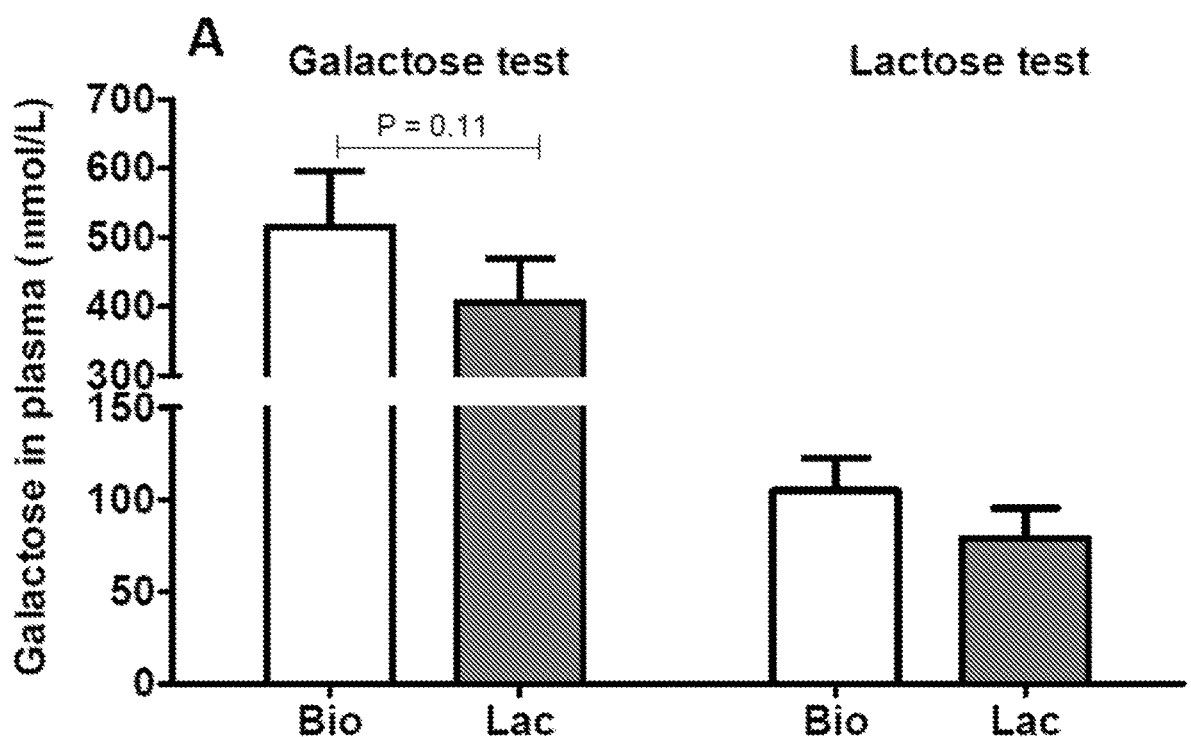
Figure 11:
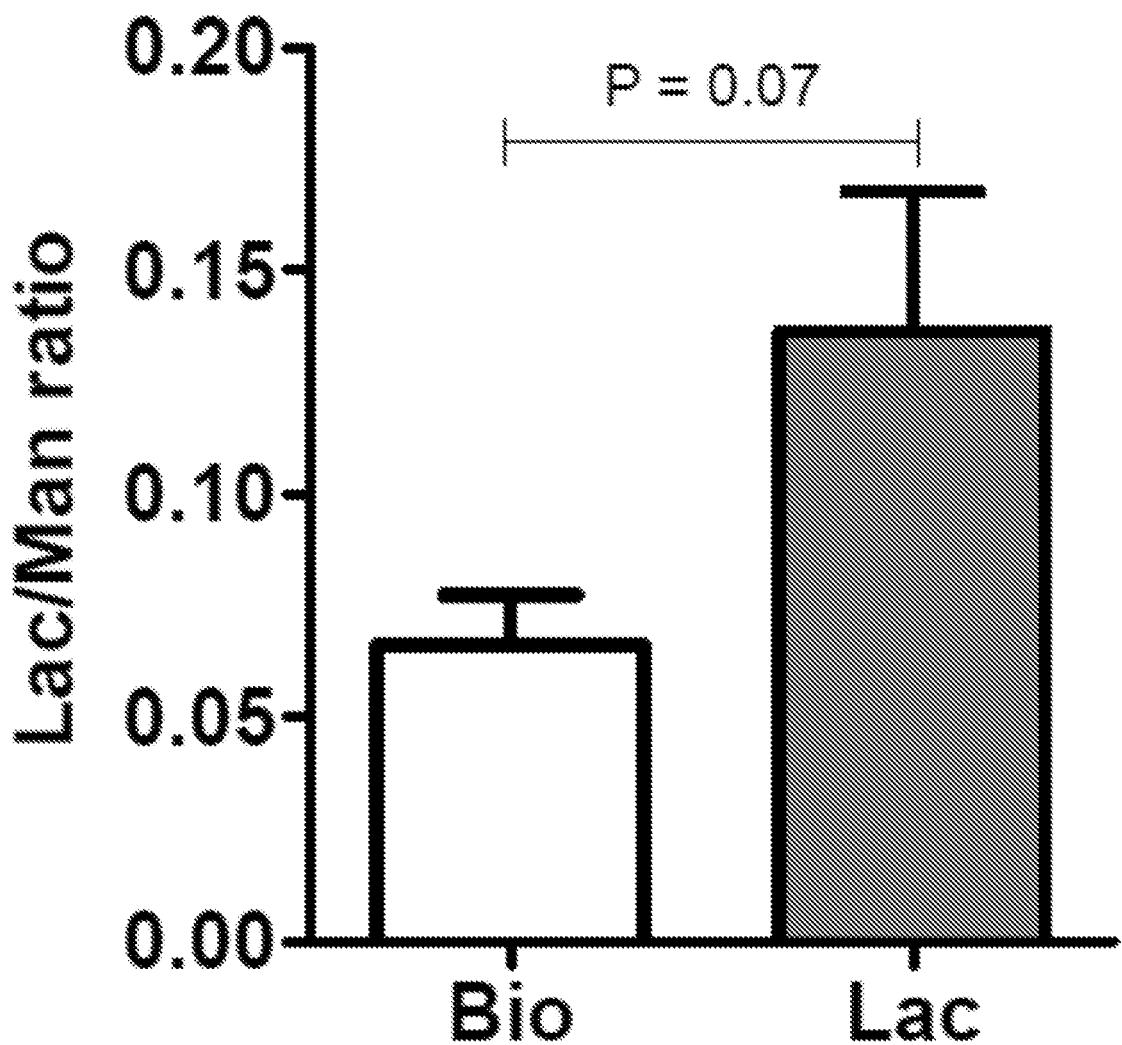

For growth factors, two WPCs had similar levels of IGF-1 (170-180 ng/g), but BioWPC contains 10 times more of TGF-beta than ConWPC (FIG. 8).

At low concentrations of 0.01-0.1 g/L, both BioWPC and ConWPC were negligibly cytotoxic whereas at 1 g/L, cytotoxicity, indicated by DNA release, was induced at higher levels by ConWPC than BioWPC (P<0.05).

BioWPC-induced cell proliferation was greater than ConWPC-induced cell proliferation at 0.01 g/L, whereas at 1 g/L, ConWPC decreased cell proliferation (P<0.05).

Example 7—Clinical Outcomes

There was no difference between the Bio and Lac groups in terms of birth weight (1014±46 g), NEC incidence (14/31), and lesion scores in the stomach (1.4±0.2), small intestinal (1.7±0.1), and colon (2.1±0.2).

The relative weights of organs and the relative length of the small intestine did not differ among groups (data now shown).

Interestingly, feeding intolerance was observed in seven pigs in the Con group and none in the Bio group.

Feeding intolerance was defined as feed-reduction or complete with-holding of feed at any time point for any reason. The decision to reduce or with-hold feeding (at each feeding time point), was based on a clinical assessment including the following criteria: signs of pain or discomfort, vomit, abdominal distension, bloody stools.

The incidence of feeding intolerance was calculated as the number of pigs in each group experiencing feed-reduction, divided by group size.

On this background there was an incidence of 44% in Lac and 0% in Bio.

Example 8—In Vivo Gut Functions and Ex Vivo Brush Border Enzyme Activities

To determine the intestinal digestive and absorptive capacity, the increment of plasma galactose in response to oral boluses of galactose and lactose was measured.

On day 3 before full EN, pigs were given a bolus (15 ml/kg) of 5% galactose via the oro-gastric feeding tubes. Heparinized blood samples were taken through the umbilical artery catheter at before and 20 min after administration of the bolus.

On day 4, pigs were given a bolus (15 ml/kg-1 body weight) of 10% lactose, and blood samples were sampled into heparin-containing tubes prior to, and at 20 min and/or 40 min after administration of the bolus. Concentrations of galactose in plasma were measured by spectrophotometry as described previously (13).

To test the intestinal permeability, pigs received an oral bolus (15 ml/kg-1 body weight) containing 5% lactulose and 2% mannitol 3 h prior to euthanasia. Post-mortem urine samples were taken to measure the concentrations of lactulose and mannitol. The ratio between lactulose and mannitol concentrations was calculated to determine the intestinal permeability.

Snap-frozen tissue samples from Prox, Mid, and Dist were homogenized in 1.0% Triton X-100 (10 ml/g tissue) using gentle MACS Dissociator (Miltenyi Biotec, Auburn, CA, USA).

After centrifugation (2000×g, 10 min, 4° C.), the supernatant was isolated and used for determining the brush border enzyme activities. The activities of lactase, maltase, sucrase, aminopeptidase N (ApN), aminopeptidase A (ApA) and dipeptidyl-peptidase IV (DPPIV) in the homogenates were analysed by spectrophotometry using corresponding sugars and peptides as substrates.

Figure 12:
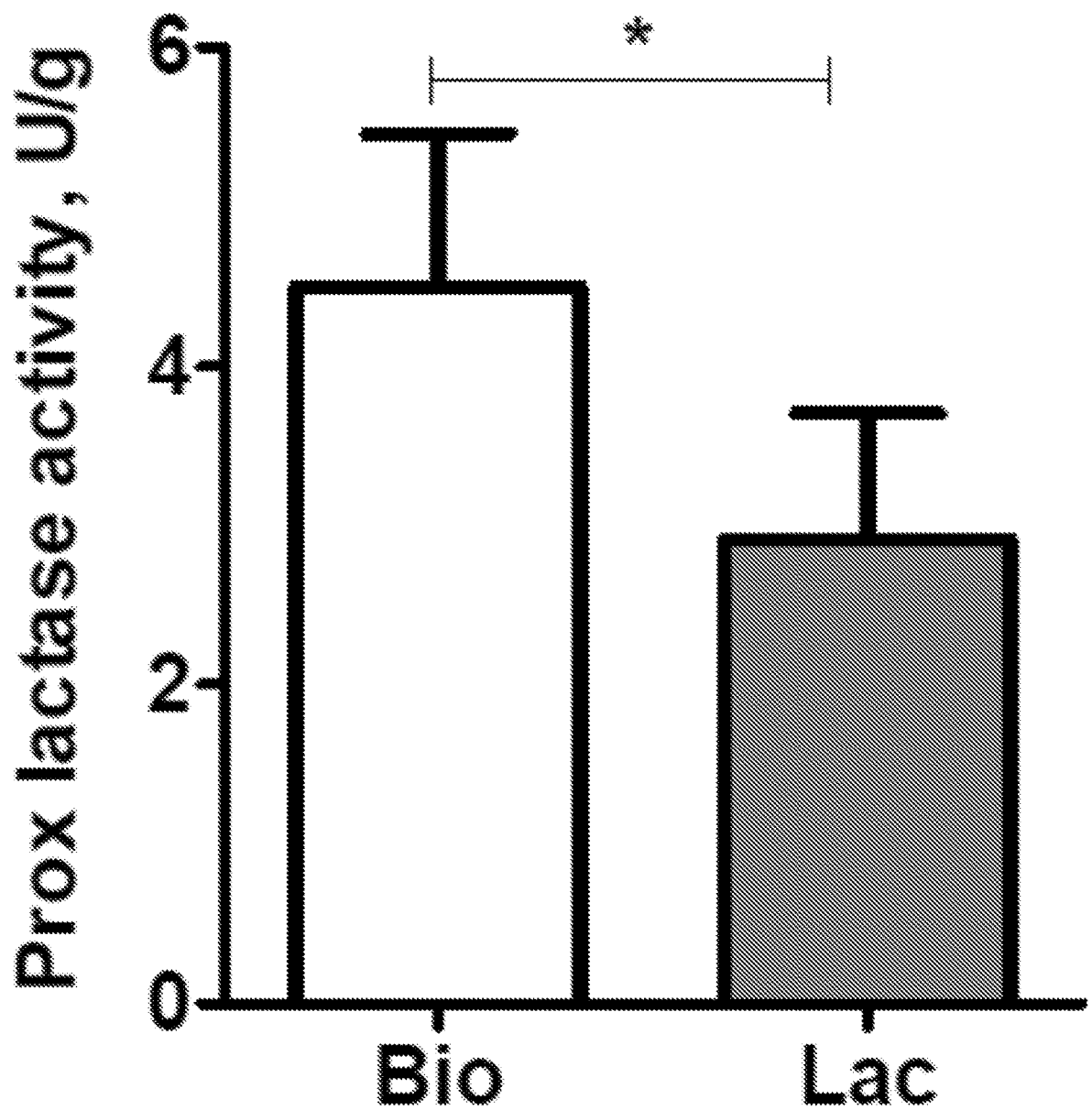

Intestinal absorptive functions measured by galactose test on day 3 tended to be higher in Bio group relative to the Con group (P=0.11, FIG. 12), whereas the function measure by lactose test on day 4 did not differ between two groups (FIG. 12).

Figure 13:
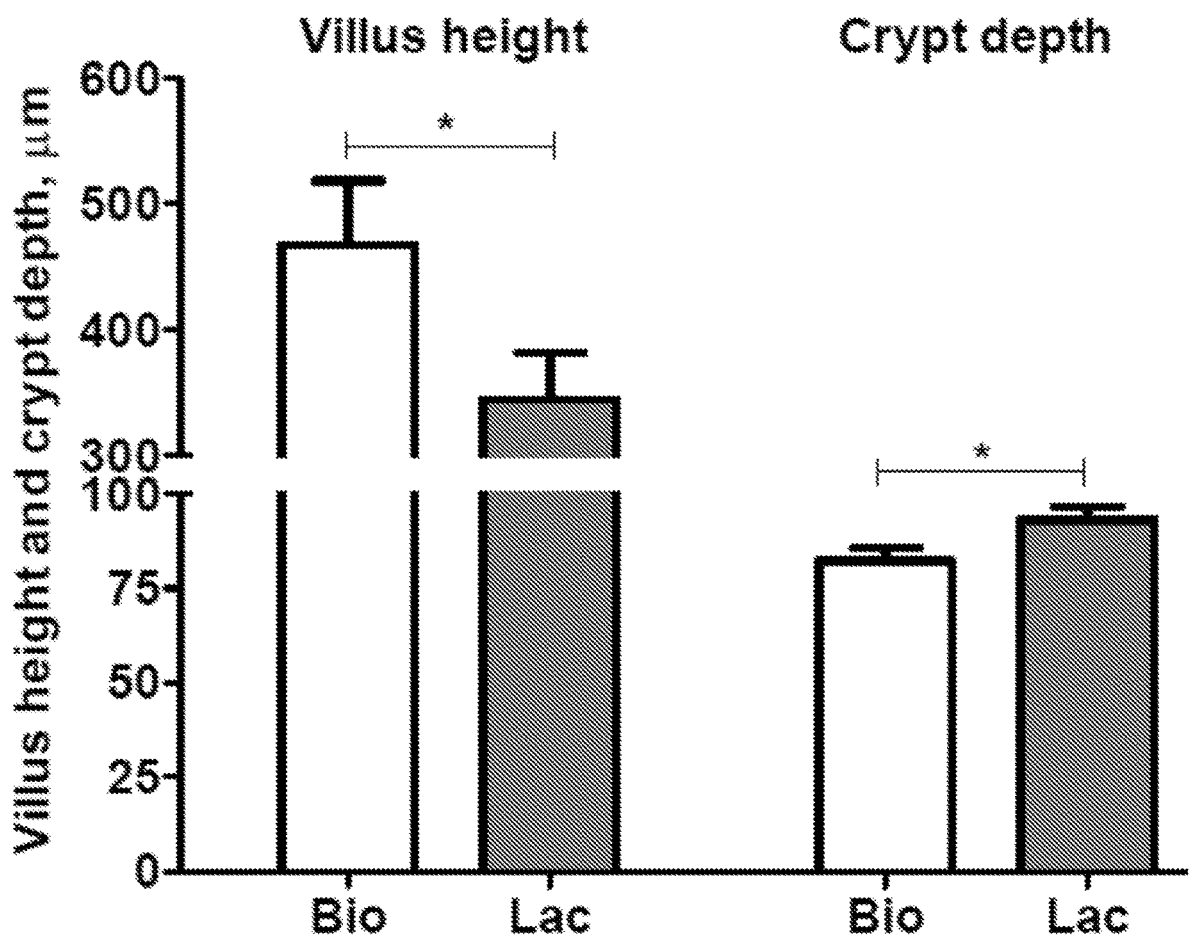

Intestinal permeability measured by lactulose/mannitol test tended to be lower in the Bio group then that in the Con group (P=0.07, FIG. 13).

Figure 14:
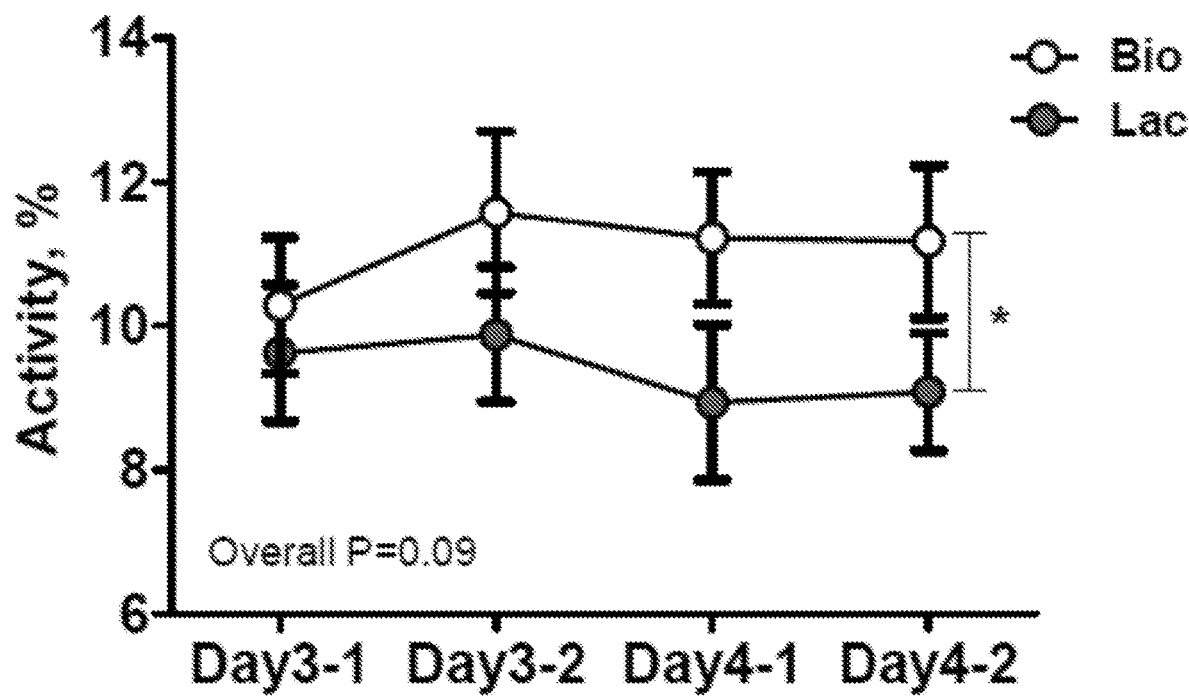

When it comes to ex vivo brush border enzyme activities, only lactase in Prox differed between two groups with higher values in the BioWPC group (P<0.05, FIG. 14).

The activity of lactase in Mid and Dist and of other brush boarder enzymes in any of the three regions did not differ between groups (data not shown).

Example 9—Intestinal Morphology and Goblet Cell Density

Paraformaldehyde-fixated tissues from Prox and Dist were embedded in paraffin, sectioned (3 µm), mounted on slides and stained with hematoxylin and eosin. Digital histology images were obtained by use of a light microscope (Ortho-plane, Leitz, Germany) and an attached camera. Mean villus height (µm), and crypt depth (µm) were measured on the digital images in ten representative vertically well-oriented villus-crypt axes in each region. (Image J 1.44p, National Institutes of Health, Bethesda, MD, USA). An average of 10 measurements in each region was used as the representative villus height or crypt depth for each pig. Clarke's fixated Dist intestine as well as colon samples were embedded in paraffin, sectioned (2 µm), mounted on slides and stained with Alcian Blue-Periodic Acid Shiff (AB-PAS) for the evaluation of goblet cell density. Slides were visualized using a light microscope (20× lens, Olympus BX45TF, Tokyo, Japan) equipped with a camera (Olympus). STEPanizer (version 1.0, company, city, country) was used to visualize the tunica mucosa including the goblet cells, and the goblet cell density was calculated as the area fraction of the total tunica mucosa that was covered by goblet cells (lamina muscularis mucosa excluded).

In the Prox region, pigs in the Bio group had increased villus height and decreased crypt depth compared with the Con group (both P<0.05, FIG. 15).

Villus height and crypt depth did not differ between two groups in the Mid and Dist regions (data not shown).

Goblet cell density did not differ between two groups neither in the Dist small intestine nor in the colon (FIG. 16).

However, when comparing pigs with Dist NEC score 1 with those with score 2, pigs scored 2 had decreased goblet cell density relative to pigs scored 1 (P<0.01, FIGS. 17 and 18).

No comparison was made for other scores due to lack of samples (only 3 pigs scored higher than 2 in the Dist small intestine).

Example 10—Effects of WPCs on Cytotoxicity and Proliferation of Porcine Immature IECs In Vitro Porcine IPEC-J2 cell line (DSMZ, Braunschweig, Germany) derived from the jejunum of a newborn pig, were used to test the effects of WPCs in vitro. Cells were cultured between passage 5-25 in advanced DMEM/F12 medium supplemented with 2% heat-inactivated fetal bovine serum, 40 U/ml penicillin, 40 µg/ml streptomycin and 2 mM Glutamax (all from Life Technologies, Naerum, Denmark), at 37° C. and 5% CO2.

Centrifuged BioWPC and HWPC solutions at 10 g/L prepared as mentioned above were sterile filtered at 0.2 µm, and diluted in serum-free culture medium to reach protein concentrations of 1, 0.1 and 0.01 g/L.

Cell cytotoxicity: cells were seeded in 96 well plates at 2×104 cells/well, and allowed to attach for 24 h. BioWPC and HWPC at 1, 0.1 and 0.01 g/L were mixed with Sytox green 5 µM (Life Technology), a non-membrane permeable dye binding to extracellular DNA, and stimulated with IECs for 6 h.

Fluorescence intensity was then measured at 485/520 nm (excitation/emission). Cell cytotoxicity was calculated by the fluorescence intensity of treatments subtracted by that of serum-free medium alone.

Cell proliferation: cells were seeded in 96 well plates at 2×104 cells/well, allowed to attach for 24 h prior to treatments with BioWPC and HWPC at 1, 0.1 and 0.01 g/L for 48 h. Cell proliferation was quantified by Celltiter 96 Aqueous One Solution Cell Proliferation Assay (Promega, Nacka, Sweden) according to the manufacturer's instructions.

Example 11—Physical Activity

Physical activity was recorded by continuous video surveillance using infrared cameras installed over each incubator and connected to an HD recorder with built-in motion detection. The digital output for each camera allowed recording of the status of the individual piglets as being either active or resting.

With the PIGLWin application (Ellegaard Systems, Faaborg Denmark), the proportion of active time was automatically registered for every hour. The cameras were turned off during any handling and contact with the pigs.

Activity recording was performed from total enteral feeding commenced on day 3 at 9:00 am and ended just before pigs were euthanized on day 5 at 9:00 am.

The proportion of active time was analyzed from means of recordings covering the day and night time, respectively.

On day 4, spontaneous motor activity was evaluated in an open field arena (1.20×1.20 m), with a video camera mounted from the ceiling (bird's eye view) during a 3-min recording period. From these recordings, piglet movements were tracked and analyzed using a commercially available software (EthoVision XT10, Noldus Information Technology, Wageningen, The Netherlands) providing information on distance travelled inside the arena. Pigs that were clinically ill on day 4 were excluded from the test.

Figure 4:
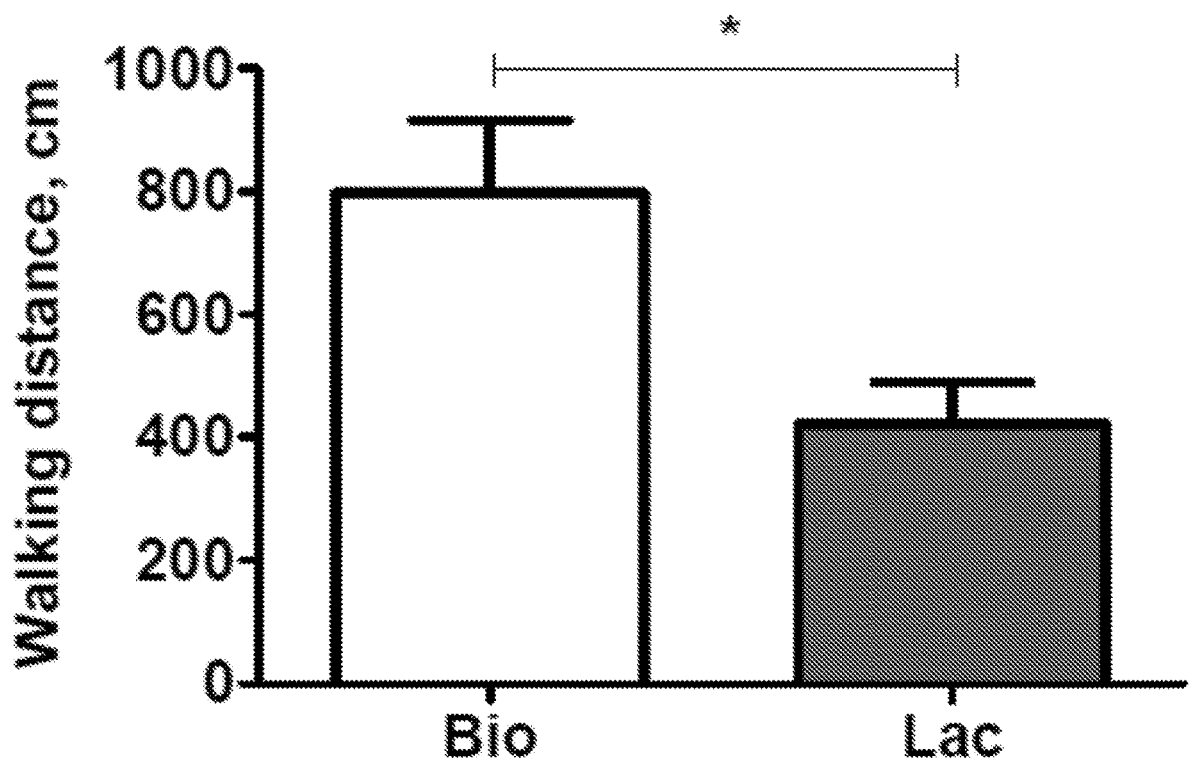
Figure 5:
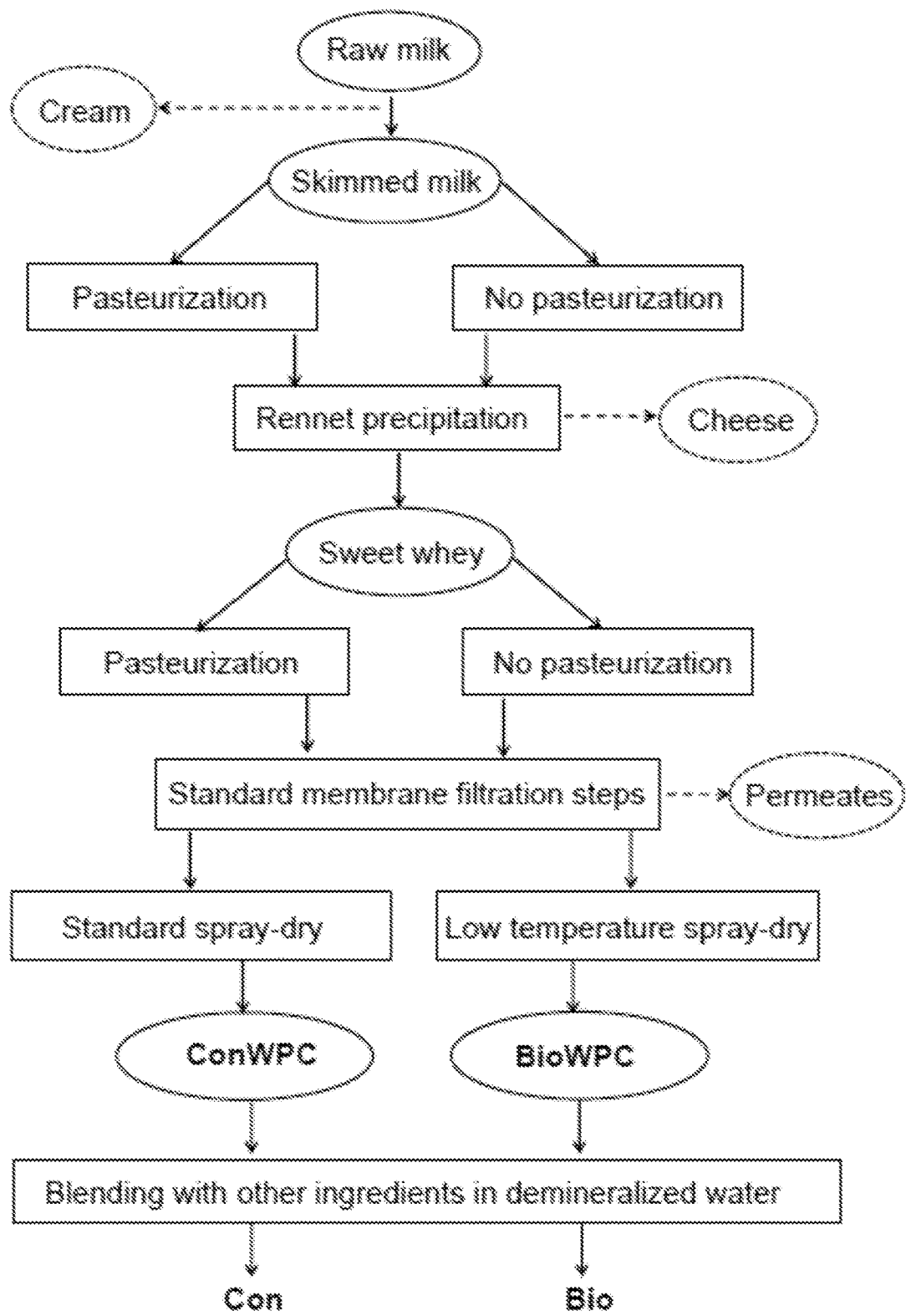
Figure 6:
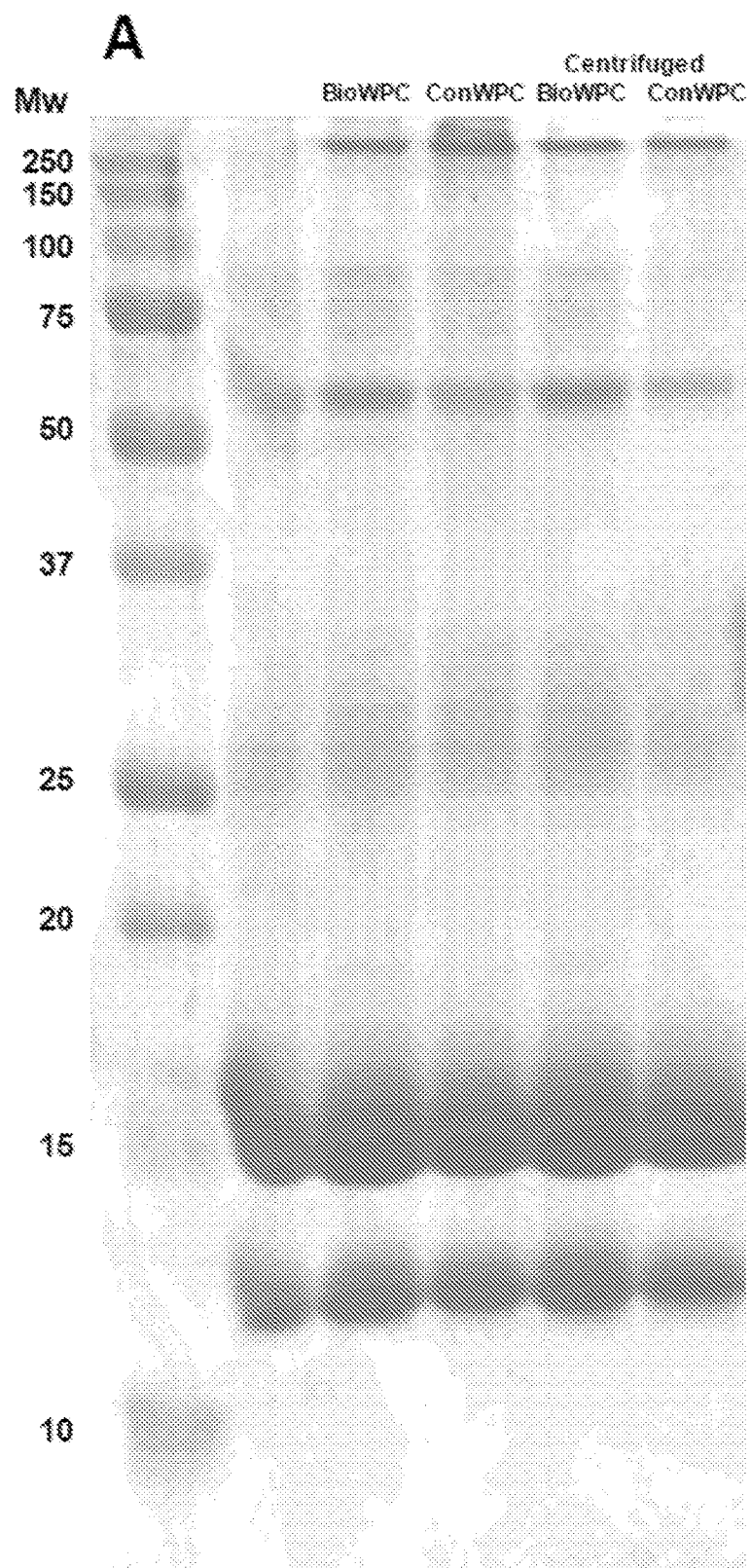

Initially, home cage activity was similar between groups, but from late day 3 and onwards, the activity level was higher in the Bio group compared to the Con group (P=0.09), and significantly increased during the last half day prior to the euthanasia (P<0.05). Further, in the open field test on day 4, Bio pigs walked almost twice the distance as that of the Con pigs (P<0.05, FIG. 4), overall supporting an increased motor activity in Bio pigs.

Result

BioWPC did not affect body and intestinal weights but significantly improved feeding tolerance compared with control pigs (P<0.01). BioWPC pigs also tended to show higher hexose absorptive capacity (P=0.09) and lower gut permeability (P=0.07).

BioWPC increased the villus height to crypt depth ratio, and proximal intestinal lactase activity (P<0.05). The time for acquisition of basic motor skills was similar between groups, and the home cage activity was initially similar between groups, but from late day 3 and onwards, the activity level was higher in the Bio group compared to the Con group (P=0.09), and significantly increased during the last half day prior to the euthanasia (P<0.05), but the BioWPC pigs tended to have more activity bouts (p=0.09), and longer activity time (p=0.10), compared with controls. The distance travelled in the open field arena was consistently longer in the BioWPC group, relative to controls (n=8, p<0.05).

CONCLUSION

The BioWPC intervention increased physical activity and locomotion in preterm pigs. This may be explained by a combination of metabolic effects, improved gut maturation or direct beneficial effects on early brain development.

REFERENCES

Anders D. Andersen, Per T. Sangild, Sara L. Munch, Eline M. van der Beek, Ingrid B. Renes, Chris van Ginneken, Gorm O. Greisen, and Thomas Thymann—Delayed growth, motor function and learning in preterm pigs during early postnatal life—Am J Physiol Regul Integr Comp Physiol 310: R481-R492, 2016.

Yanqi Li, Mette V. Østergaard, Pingping Jiang, Dereck E. W. Chatterton, Thomas Thymann, Anne S. Kvistgaard, and Per T. Sangild—Whey Protein Processing Influences Formula-Induced Gut Maturation in Preterm Pigs—The Journal of Nutrition 2013/09/18/jn.113.182931

The invention claimed is:

1. A method for producing a mildly-heated treated bioactive sweet whey WPC80 preparation comprising a high level of bioactive compounds with reduced denaturation and aggregation, said method comprising the sequential steps of:
   a) providing a sweet whey;
   b) applying a first heat-treatment of the sweet whey between 60° C. and 68° C. for between 10 and 20 seconds, wherein the heat treatment is for reducing cheese starter culture bacterial growth and preventing further pH drop in the whey;
c) cooling the sweet whey to a temperature of 5° C. to 18° C.;
d) applying a separation and/or concentration step at 5° C. to 18° C., which separation is ultrafiltration and which concentration is reverse osmosis or nano filtration to obtain WPC35;
e) applying a micro filtration on the retentate from step d) to prevent particles from entering into the permeate, wherein the particles are sediment, algae, protozoa or large bacteria;
f) applying a separation on the permeate from step e) at 5° C. to 18° C. to obtain WPC80, and wherein, the separation is ultrafiltration;
g) applying a second heat-treatment of between 60° C. and 65° C. for between 10 and 20 seconds on the retentate of step f);
h) optionally, cooling the product obtained in g) to less than 15° C. for storage of the bioactive sweet whey WPC80 preparation; and
i) optionally drying said product, thereby obtaining a dried bioactive sweet whey WPC80 preparation.

2. The method of claim 1, wherein the separation in step d) is ultra-filtration.

3. The method of claim 1, wherein the microfiltration is performed using a ceramic membrane with a pore size of 0.5 to 2 µm.

4. The method of claim 1, wherein the concentration in step d) is reverse osmosis or nano filtration.

5. The method of claim 1, wherein the sweet whey is derived from a milk base that has not been exposed to standard industrial processing steps selected from the group consisting of thermal processing, ultra-high temperature processing (UHT), hydrolysis and irradiation.

6. The method of claim 1, wherein the heat treatment under step b) is applied at a temperature of 60 to 67° C.

7. The method of claim 1, wherein the heat treatment under step b) is applied for less than 19 seconds.

8. The method of claim 1, wherein the method comprises cooling the preparation obtained in g) to less than 15° C.

9. The method of claim 1, wherein the method comprises drying said preparation.

10. The method of claim 1, wherein the microfiltration is performed using a ceramic membrane with a pore size of 0.8 to 1.5 µm.

11. The method of claim 1, wherein the microfiltration is performed using a ceramic membrane with a pore size of 1.0 to 1.5 µm.

12. The method of claim 1, wherein the microfiltration is performed using a ceramic membrane with a pore size of 1.0 to 2 µm.

13. The method of claim 1, wherein the heat treatment under step b) is applied at a temperature of 60 to 63 ° C.

14. The method of claim 1, wherein the heat treatment under step b) is applied for less than 15 seconds.

* * * * *